(12) United States Patent
Bodmer et al.

(10) Patent No.: US 9,186,093 B2
(45) Date of Patent: Nov. 17, 2015

(54) COMPOSITIONS AND METHODS FOR SCREENING CARDIOACTIVE DRUGS

(75) Inventors: Rolf Bodmer, La Jolla, CA (US); Karen Ocorr, La Jolla, CA (US); Martin Fink, Feldkurchen (AT)

(73) Assignees: THE REGENTS OF THE UNIVERSITY OF CALIFORNIA, Oakland, CA (US); BURNHAM INSTITUTE FOR MEDICAL RESEARCH, La Jolla, CA (US)

(*) Notice: Subject to any disclaimer, the term of this patent is extended or adjusted under 35 U.S.C. 154(b) by 1608 days.

(21) Appl. No.: 12/544,465

(22) Filed: Aug. 20, 2009

(65) Prior Publication Data
US 2010/0049064 A1 Feb. 25, 2010

Related U.S. Application Data

(60) Provisional application No. 61/189,680, filed on Aug. 20, 2008.

(51) Int. Cl.
| | | |
|---|---|---|
| A61B 6/00 | (2006.01) | |
| A61B 5/107 | (2006.01) | |
| G01N 33/50 | (2006.01) | |
| A61B 5/00 | (2006.01) | |
| A61B 8/08 | (2006.01) | |

(52) U.S. Cl.
CPC .......... *A61B 5/1075* (2013.01); *G01N 33/5088* (2013.01); *A61B 5/1076* (2013.01); *A61B 5/4519* (2013.01); *A61B 8/0883* (2013.01); *A61B 2503/40* (2013.01)

(58) Field of Classification Search
CPC ............. A61B 2503/40; A61B 5/1075; A61B 5/1076; A61B 5/4519; A61B 8/0883; G01N 33/5088
USPC ........... 600/347–469, 473–480; 382/128–132
See application file for complete search history.

(56) References Cited

U.S. PATENT DOCUMENTS

| | | | | |
|---|---|---|---|---|
| 4,945,916 | A * | 8/1990 | Kretschmer et al. | 600/484 |
| 5,047,846 | A * | 9/1991 | Uchiyama et al. | 348/61 |
| 6,825,780 | B2 * | 11/2004 | Saunders et al. | 341/50 |
| 7,087,021 | B2 * | 8/2006 | Paternostro | 600/443 |
| 7,196,317 | B1 * | 3/2007 | Meissner et al. | 250/227.14 |
| 7,764,818 | B2 * | 7/2010 | Sumanaweera et al. | 382/131 |
| 7,992,573 | B2 * | 8/2011 | Wilson et al. | 128/899 |
| 8,320,711 | B2 * | 11/2012 | Altmann et al. | 382/294 |
| 2002/0161302 | A1 * | 10/2002 | Paternostro | 600/476 |
| 2003/0197629 | A1 * | 10/2003 | Saunders et al. | 341/50 |
| 2005/0104752 | A1 * | 5/2005 | Saunders et al. | 341/50 |

(Continued)

OTHER PUBLICATIONS

Thom et al., Heart disease and stroke statistics—2006 update: a report from the American Heart Association Statistics Committee and Stroke Statistics Subcommittee. Circulation Feb. 14, 2006;113(6):e85-151.

(Continued)

*Primary Examiner* — Sanjay Cattungal
(74) *Attorney, Agent, or Firm* — Sam K. Tahmassebi

(57) ABSTRACT

We have developed a reduced *Drosophila* heart preparation in which dissection of the fly heart removes nervous system input and reveals its inherent myogenic activity, which can be preserved for several hours. High speed image capture combined with computer-based analytical packages allows us to generate the equivalent of M-mode traces obtained from ultrasounds of human hearts.

7 Claims, 6 Drawing Sheets

(56) References Cited

U.S. PATENT DOCUMENTS

| | | | |
|---|---|---|---|
| 2005/0113678 A1* | 5/2005 | Villard et al. | 600/425 |
| 2006/0036164 A1* | 2/2006 | Wilson et al. | 600/424 |
| 2007/0014446 A1* | 1/2007 | Sumanaweera et al. | 382/128 |
| 2007/0015964 A1* | 1/2007 | Eversull et al. | 600/114 |
| 2007/0177772 A1* | 8/2007 | Fujii et al. | 382/115 |
| 2007/0293724 A1* | 12/2007 | Saadat et al. | 600/156 |
| 2008/0039715 A1* | 2/2008 | Wilson et al. | 600/424 |
| 2008/0319317 A1* | 12/2008 | Kamiyama et al. | 600/443 |
| 2009/0124908 A1* | 5/2009 | Rafter et al. | 600/458 |
| 2009/0148012 A1* | 6/2009 | Altmann et al. | 382/128 |
| 2010/0298716 A1* | 11/2010 | Villard et al. | 600/476 |

OTHER PUBLICATIONS

Vinereanu et al., Estimation of Global Left Ventricular Function from the Velocity of Longitudinal Shortening. Echocardiography Apr. 2002;19(3):177-185.

Wang et al., Two-Photon Calcium Imaging Reveals an Odor-Evoked Map of Activity in the Fly Brain. Cell Jan. 24, 2003;112(2):271-282.

Wessels and Bodmer, Screening assays for heart function mutants in Drosophila. Biotechniques Jul. 2004;37(1):58-60 ,62, 64, 66 passim.

Wessells et al., Insulin regulation of heart function in aging fruit flies. Nat. Genet. Dec. 2004;36(12):1275-1281.

White et al., Effects of deuterium oxide and temperature on heart rate in Drosophila melanogaster. J. Comp. Physiol. B 1992;162(3):278-283.

Wolf et al., Drosophila as a model for the identification of genes causing adult human heart disease. Proc. Natl. Acad. Sci. USA Jan. 31, 2006;103(5):1394-1399.

Wolf et al., Atrial Fibrillation as an Independent Risk Factor for Stroke: The Framingham Study. Stroke Aug. 1991;22(8):983-988.

Yeung and Greenwood, Electrophysiological and functional effects of the KCNQ channel blocker XE991 on murine portal vein smooth muscle cells. Br. J. Pharmacal. Oct. 2005;146(4):585-595.

Zingman et al., Kir6.2 is required for adaptation to stress. Proc. Natl. Acad. Sci. USA Oct. 1, 2002;99(20):13278-13283.

Akasaka et al., The ATP-sensitive potassium (KATP) channel-encoded dSUR gene is required for Drosophila heart function and is regulated by tinman. Proc. Natl. Acad. Sci. USA Aug. 8, 2006;103(32):11999-12004.

Ashton et al., Quantitative Trait Loci for the Monoamine-Related Traits Heart Rate and Headless Behavior in Drosophila melanogaster. Genetics Jan. 2001;157(1):283-294.

Bodmer, Heart Development in Drosophila and Its Relationship to Vertebrates. Trends Cardiovasc. Med. Jan.-Feb. 1995;5(1):21-28.

Brand and Perrimon, Targeted gene expression as a means of altering cell fates and generating dominant phenotypes. Development Jun. 1993;118(2):401-415.

Cleland et al., The Development of Stable Protein Formulations: A Close Look at Protein Aggregation, Deamidation, and Oxidation. Crit Rev Ther Drug Carrier Syst. 1993;10(4):307-377.

Cripps and Olson, Control of Cardiac Development by an Evolutionarily Conserved Transcriptional Network. Dev Biol. Jun. 1, 2002;246(1):14-28.

Curtis et al., Morphology of the Pupal Heart, Adult Heart, and Associated Tissues in the Fruit Fly, Drosophila melanogaster. J. Morphol. Jun. 1999;240(3):225-235.

Dowse et al., A congenital heart defect in Drosophila caused by an action-potential mutation. J. Neurogenet. Dec. 1995;10(3):153-168.

Dulcis and Levine, Glutamatergic Innervation of the Heart Initiates Retrograde Contractions in Adult Drosophila melanogaster. J. Neurosci Jan. 12, 2005;25(2):271-280.

Dulcis et al., Role of the Neuropeptide CCAP in Drosophila Cardiac Function. J. Neurobiol. Sep. 5, 2005;64(3):259-274.

Furberg et al., Prevalence of Atrial Fibrillation in Elderly Subjects (The Cardiovascular Health Study). Am. J. Cardiol. Aug. 1, 1994;74(3):236-241.

Garrity et al., The heartstrings mutation in zebrafish causes heart/fin Tbx5 deficiency syndrome. Development Oct. 2002;129(19):4635-4645.

Gligorova and Agrusta, Pacing Stress Echocardiography. Cardiovasc. Ultrasound Dec. 9, 2005;3:36.

Gowda et al., History of the Evolution of Echocardiography. Int. J. Cardiol. Oct. 2004 97:1-6.

Grunnet et al., Functional assessment of compound mutations in the KCNQ1 and KCNH2 genes associated with long QT syndrome. Heart Rhythm Nov. 2005;2(11):1238-1249.

Gu and Singh, Pharmacological analysis of heartbeat in Drosophila. J. Neurobiol. Nov. 1995;28(3):269-280.

Harvey, NK-2 Homeobox Genes and Heart Development. Dev. Biol. Sep. 15, 1996;178(2):203-216.

Jentsch, Neuronal KCNQ potassium channels: physiology and role in disease. Nat. Rev. Neurosci. Oct. 2000;1(1):21-30.

Ji et al., Onset of Cardiac Function During Early Mouse Embryogenesis Coincides With Entry of Primitive Erythroblasts Into the Embryo Proper. Circ. Res. Feb. 7, 2003;92(2)133-135.

Johnson et al., Modulation of the cardiac pacemaker of Drosophila: cellular mechanisms. J. Comp. Physiol. B Apr. 2002;172(3):227-236.

Johnson et al., Modulation of Drosophila heartbeat by neurotransmitters. J. Comp. Physiol. B Feb. 1997;167(2):89-97.

Johnson et al., Native and heterologous neuropeptides are cardioactive in Drosophila melanogaster. J. Insect Physiol. Aug. 1, 2000;46(8):1229-1236.

Johnston et al., FlyGEM, a full transcriptome array platform for the Drosophila Community. Genome Biol. 2004;5(3):R19.

Jose and Collison, The normal range and determinants of the intrinsic heart rate in man. Cardiovasc. Res. Apr. 1970;4(2):160-167.

Lakatta and Levy, Arterial and Cardiac Aging: Major Shareholders in Cardiovascular Disease Enterprises Part II: The Aging Heart in Health: Links to Heart Disease. Circulation Jan. 21, 2003;107(2):346-354.

Lakatta, Age-associated Cardiovascular Changes in Health: Impact on Cardiovascular Disease in Older Persons. Heart Fail. Review Jan. 2002;7(1):29-49.

Lakatta, Cardiovascular Ageing in Health Sets the Stage for Cardiovascular Disease. Heart Lung Circ. 2002;11(2):76-91.

Lalevee et al., Control of Cardiac Rhythm by ORK1, a Drosophila Two-Pore Domain Potassium Channel. Curr. Biol. Aug. 8, 2006;16(15):1502-1508.

Lee et al., Loss of Preconditioning by Attenuated Activation of Myocardial ATP-Sensitive Potassium Channels in Elderly Patients Undergoing Coronary Angioplasty. Circulation Jan. 22, 2002;105(3): 334-340.

Maurer et al., Diastolic Dysfunction: Can it Be Diagnosed by Doppler Echocardiography? J. Am. Coll. Cardiol. 44: Oct. 19, 2004;44(8):1543-1549.

Molina and Cripps, Ostia, the inflow tracts of the Drosophila heart, develop from a genetically distinct subset of cardial cells. Mech. Dev. Nov. 2001;109(1):51-59.

Monier et al., Steroid-dependent modification of Hox function drives myocyte reprogramming in the Drosophila heart. Development Dec. 2005;132(23):5283-5293.

Ocorr et al., Genetic Control of Heart Function and Aging in Drosophila. Trends Cardiovasc. Med. Jul. 2007;17(5):177-182.

Ocorr et al., KCNQ potassium channel mutations cause cardiac arrhythmias in Drosophila that mimic the effects of aging. Proc. Natl. Acad. Sci. USA Mar. 6, 2007;104(10):3943-3948.

Papaefthmiou and Theophilidis, An In Vitro Method for Recording the Electrical Activity of the Isolated Heart of the Adult Drosophila melanogaster. In Vitro Cell Dev. Biol. Anim. Jul.-Aug. 2001;37(7):445-449.

Paternostro et al., Age-Associated Cardiac Dysfunction in Drosophila melanogaster. Circ. Res. May 25, 2001;88(10):1053-1058.

Porter and Rivkees, Ontogeny of humoral heart rate regulation in the embryonic mouse. Am. J. Physiol. Regul. Integr. Comp. Physiol. Aug. 2001;281(2):R401-R407.

Priori and Napolitano, Genetics of Cardiac Arrhythmias and Sudden Cardiac Death. Ann. N.Y. Acad. Sci. May 2004;1015:96-110.

Priori, Inherited Arrhythmogenic Diseases: The Complexity Beyond Monogenic Disorders. Circ. Res. Feb. 6, 2004;94(2):140-145.

(56) References Cited

OTHER PUBLICATIONS

Reaume et al., Motor neurons in Cu/Zn superoxide dismutase-deficient mice develop normally but exhibit enhanced cell death after axonal injury. Nat Genet. May 1996;13(1):43-47.

Robbins, KCNQ potassium channels: physiology, pathophysiology, and pharmacology. Pharmacol. Ther. Apr. 2001;90(1):1-19.

Roberts, Genomics and Cardiac Arrhythmias. J Am Coll Cardiol. Jan. 3, 2006;47(1):9-21.

Roden, Human Genomics and Its Impact on Arrhythmias. Trends Cardiovasc. Med. Apr. 2004;14(3):112-116.

Sanguinetti et al., Coassembly of K(V)LQT1 and minK (IsK) proteins to form cardiac I(Ks) potassium channel. Nature Nov. 7, 1996;384(6604):80-83.

Sanguinetti and Tristani-Firouzi, hERG potassium channels and cardiac Arrhythmia. Nature Mar. 23, 2006;440(7083):463-469.

Sanyal et al., Conditional mutations in SERCA, the Sarco-endoplasmic reticulum Ca2+-ATPase, alter heart rate and rhythmicity in *Drosophila*. J. Comp. Physiol. B Mar. 2006;176(3):253-263.

Seidman and Seidman, Transcription factor haploinsufficiency: when half a loaf is not enough. J. Clin. Invest. Feb. 2002;109(4):451-455.

Senio and Miki, Physiological and pathophysiological roles of ATP-sensitive K+ channels. Prog. Biophys. Mol. Biol. Feb. 2003;81(2):133-176.

Singleton and Woodruff, The Osmolarity of Adult *Drosophila* Hemolymph and Its Effect on Oocyte-Nurse Cell Electrical Polarity. Dev. Biol. Jan. 1994;161(1):154-167.

Strobel et al., Nonpharmacologic Validation of the Intrinsic Heart Rate in Cardiac Transplant Recipients. J. Interv. Card. Electrophysiol. Mar. 1999;3(1):15-18.

\* cited by examiner

COMPOSITIONS AND METHODS FOR SCREENING CARDIOACTIVE DRUGS

CROSS-REFERENCE TO RELATED APPLICATIONS

This application claims priority from U.S. Provisional Application Ser. No. 61/189,680 filed Aug. 20, 2008.

STATEMENT OF GOVERNMENT RIGHTS

This invention was made with Government support under grants no. HL54732 and HL084949 awarded by the National Institutes of Health. The Government has certain rights in the invention.

TECHNICAL FIELD

The present invention relates to methods for screening cardioactive drugs.

BACKGROUND INFORMATION

Despite recent advances in preventing deaths related to cardiac disorders, cardiovascular disease (CVD) remains the leading cause of death in industrialized countries (Thom et al., Circulation 113:e-85-151, 2006). As life expectancy increases, the population profiles in these countries are changing to include increasing numbers of middle-aged and elderly individuals. In both industrialized countries as well as in countries that are becoming industrialized a number of other factors such as altered life styles, urbanization, and as yet unidentified genetic and environmental factors combine to compound the effects of aging on CVD (Lakatta, Heart Fail. Review 7:29-49, 2002). Cardiac arrhythmias are common in patients with cardiac dysfunction and some forms of arrhythmias, such as atrial fibrillations, increase with age (Lakatta and Levy, Circulation 107:346-354). However, the mechanisms underlying arrhythmias and heart failure have remained elusive, in part, because heart diseases in humans are associated with a complex array of hormonal, physiological, genetic and biochemical abnormalities. In addition, vertebrate heart structure is very complex, as is the process of its embryological development from a simple tube-like structure.

Since heart function is so essential for survival, it is difficult to study strongly deleterious heart abnormalities in vertebrate systems. Increasing insights into the molecular genetics of CVD suggest that the genetic heterogeneity underlying heart disease is very high (Priori and Napolitano, Ann. N.Y. Acad. Sci. 1015:96-110, 2004). This aspect of heart disease is difficult to examine in vertebrate systems. The relatively long lifespan of mammalian systems precludes a simple approach to elucidate the aging-related factors contributing to the genesis and facilitation of arrhythmic disorders. More importantly, hereditary and/or acquired arrhythmic disorders in mammalian hearts usually lead to sudden death, making the study of genetic interactions or polygenetic disorders extremely difficult in mammals (Roberts, J. Am. Coll. Card. 47:9-21, 2006). Thus *Drosophila*, a system that is already a powerful genetic model, provides unique advantages for studying heart aging and disease.

The basic mechanisms of heart development and function are conserved between *Drosophila* and vertebrates (Bodmer, Trends Cardiovasc. Med. 5:21-27, 1995; Harvey, Dev. Biol. 178:203-216, 1996; Bodmer and Frasch, in *Heart Development*, eds. Rosenthal and Harvey (Academic Press, New York), pp. 65-90, 1999; Cripps and Olson, Dev. Biol. 246:14-28, 2002; Seidman and Seidman, J. Clin. Investig. 109:451-455, 2002; Bodmer et al., in *Comprehensive Insect Science*, edited by L. Gilbert, Latrau, K., and Gill S. (Elsevier, Amsterdam, 2005), Vol. 2, pp. 199). We have begun to use the fly heart and the power of *Drosophila* genetics to understand the genetic and molecular mechanisms underlying aging of cardiac tissue and their contribution to cardiac disorders and arrhythmias.

A number of genetic defects that contribute to arrhythmogenic disorders have been identified in humans. Many of these identified genes encode $K^+$ channels such as the Human Ether-a-go-go Related Gene (HERG), which encodes a channel underlying the rapid phase of cardiac repolarization ($I_{Kr}$), as well as the KCNQ1 gene, which encodes a subunit of a $K^+$ channel responsible for the slower repolarizing current ($I_{Ks}$) (for reviews see Jentsch, Nat. Rev. Neurosci. 1:21-30, 2000; Robbins, Pharmacol. Ther. 90:1-9, 2001; Sanguinetti, Nature 440:463-469, 2006). Mutations in these $K^+$ channels commonly lead to a loss or decrease in channel function resulting in reduced cardiac repolarization and prolonged cardiac action potentials that increase the risk of early after-depolarization (EAD). In humans, this prolonged repolarization phase, which manifests as a prolonged QT interval on the surface electrocardiograms (ECGs), is known as long QT syndrome (LQTS); it is associated with increased risk of Torsades des Pointes (TdP) ventricular arrhythmias, which would cause recurrent syncope or sudden cardiac death. Age, environmental stressors, exercise, genetic modifiers and some commonly prescribed drugs have also been shown to produce arrhythmic disorders such as LQTS, but the complex interactions between these acquired and inherited factors for arrhythmogenesis remain to be determined (Priori and Tristani-Firouzi, Circ. Res. 94:140-145, 2004; Roberts, J. Am. Coll. Card. 47:9-21, 2006).

A systematic genetic analysis will be required to identify genetic variations (polymorphisms) in known genes as well as to identify novel genes and gene products that influence the risk of arrhythmias. Because susceptibility to drug-induced LQTS is likely to have a genetic basis, a functional assessment of genetic mutations and identification of interactions between genes that contribute to arrhythmias would permit more appropriate drug administration to patients with CVD (Grunnet et al., Heart Rhythm 2:1238-1249, 2005).

Thus, there is a need for improved methods and compositions for determining the effects of various genes, and mutations in these genes, on heart function. Moveover, there is a need for improved methods and compositions for screening drugs and other treatments for their effects on heart function. The present invention meets this and other needs.

SUMMARY OF THE INVENTION

Because oxygen distribution in the fruit fly is carried out by an independent tracheal system, genetic manipulation of cardiac expressed genes that compromise heart function are not immediately lethal (Wessels et al., Nat. Genet. 36:1275-1281, 2004), permitting the characterization of severe abnormalities in heart physiology, including those arising from single-gene defects, such as those in ion channels. Thus, this system allows us to identify and characterize genes that contribute to normal heart function, to analyze the effects of genetic aberrations, to perform structure-function studies in a functioning organ, and to examine the genetic basis for functional deterioration with age. In addition, this system is useful for screening drugs that affect heart function.

We have developed a *Drosophila* heart preparation that allows us to quantify and describe a number of parameters that are important in heart function. This methodology combines high speed optical recording of beating hearts with a robust, semi-automated analysis algorithm that is able to quantify heart beat parameters such as heart rate, diastolic and systolic intervals, systolic and diastolic diameters, percent fractional shortening, and contraction wave velocity on a beat-to-beat basis. In addition, our algorithm quantifies cardiac arrhythmicity, which increases as flies age. Our algorithm was also able to analyze optical recordings of hearts from larval zebrafish and 8d mouse embryos. Using this methodology we were able, for example, to document age-dependent changes in heart function in to different laboratory fly strains (yw and $w^{1118}$). We were also able to detect effects of a single mutant allele on heart function in tbx5 heterozygote mutant zebrafish.

Accordingly, the present invention provides compositions comprising (a) an excised, denervated *Drosophila* heart that retains myogenic activity, and (b) a physiologically acceptable hemolymph fluid in contact with the semi-intact *Drosophila* heart. In one such embodiment, the *Drosophila* heart is denervated by removal of fat bodies that surround the heart in an intact *Drosophila* fly. In another such embodiment, the *Drosophila* fly comprises a mutation in a gene that affects heart function in the fly.

According to another embodiment of the invention, methods are provided for making an excised, denervated *Drosophila* heart that retains myogenic activity comprising: (a) excising from a *Drosophila* fly a *Drosophila* heart preparation that comprises fat bodies; and (b) removing the fat bodies. In one such embodiment the method comprises removing the fat bodies by suction.

According to another embodiment of the invention, methods are provided for testing a compound for cardioactivity comprising: (a) providing a composition comprising an excised, denervated *Drosophila* heart that retains myogenic activity, and a physiologically acceptable hemolymph fluid in contact with said *Drosophila* heart; (b) contacting the composition with the compound; and (c) assessing the effect of the compound on the myogenic activity of the semi-intact *Drosophila* heart. In one such embodiment the method comprises assessing the effect of the compound on myogenic activity of the semi-intact *Drosophila* heart by producing images of the semi-intact *Drosophila* heart and analyzing the images. In another such embodiment, the method comprises determining a member of the group consisting of heart period, heart rate, diastolic interval, systolic interval, standard deviation of heart period, standard deviation of heart rate, standard deviation of diastolic interval, standard deviation of systolic interval, percent fractional shortening of heart contraction, arrhythmia index, velocity of heart muscle contraction, and directionality of heart muscle contraction.

According to another embodiment of the invention, methods are provided for analyzing heart movement comprising: (a) producing a plurality of images of the heart as it beats; (b) identifying changes in overall light intensity in said plurality of images to determine whether the heart is in a contracted or relaxed condition; (c) detecting movement of the heart by comparing intensity changes in individual pixels from one of said plurality of said images to another of said images; and (d) identifying a pause between contraction and relaxation movements of the heart. In one such embodiment, the method comprises using a Frame Brightness algorithm to identify said changes in overall light intensity in said plurality of images to determine whether the heart is in the contracted or relaxed condition. In another such embodiment, the method comprises using a Changing Pixel Intensity algorithm to detect said movement of the heart by comparing intensity changes in individual pixels from one of said plurality of said images to another of said images. In another such embodiment, the method comprises using an output from a Frame Brightness algorithm to inform the Changing Pixel Intensity algorithm regarding whether the heart is in the contracted or relaxed condition. In another such embodiment, the method comprises producing a movie of the heart as it beats, wherein the movie comprises said plurality of images. In another such embodiment, the method comprises determining a member of the group consisting of heart period, heart rate, diastolic interval, systolic interval, standard deviation of heart period, standard deviation of heart rate, standard deviation of diastolic interval, standard deviation of systolic interval, percent fractional shortening of heart contraction, arrhythmia index, velocity of heart muscle contraction, and directionality of heart muscle contraction. In another such embodiment, the heart is selected from the group consisting of a *Drosophila* heart, a zebrafish larval heart, a mouse embryo heart, and a human heart. In another such embodiment, the heart is an excised, denervated *Drosophila* heart that retains myogenic activity.

According to another embodiment of the invention, methods are provided for analyzing activity of a heart comprising: (a) producing an echocardiogram of the heart; (b) identifying changes in overall light intensity in said plurality of images to determine whether the heart is in a contracted or relaxed condition; (c) detecting movement of the heart by comparing intensity changes in individual pixels from one of said plurality of said images to another of said images; and (d) identifying a pause between contraction and relaxation movements of the heart. According to one such embodiment, the heart is a human heart. According to another such embodiment, the method comprises identifying an arrythmicity of the heart.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Figure 1:
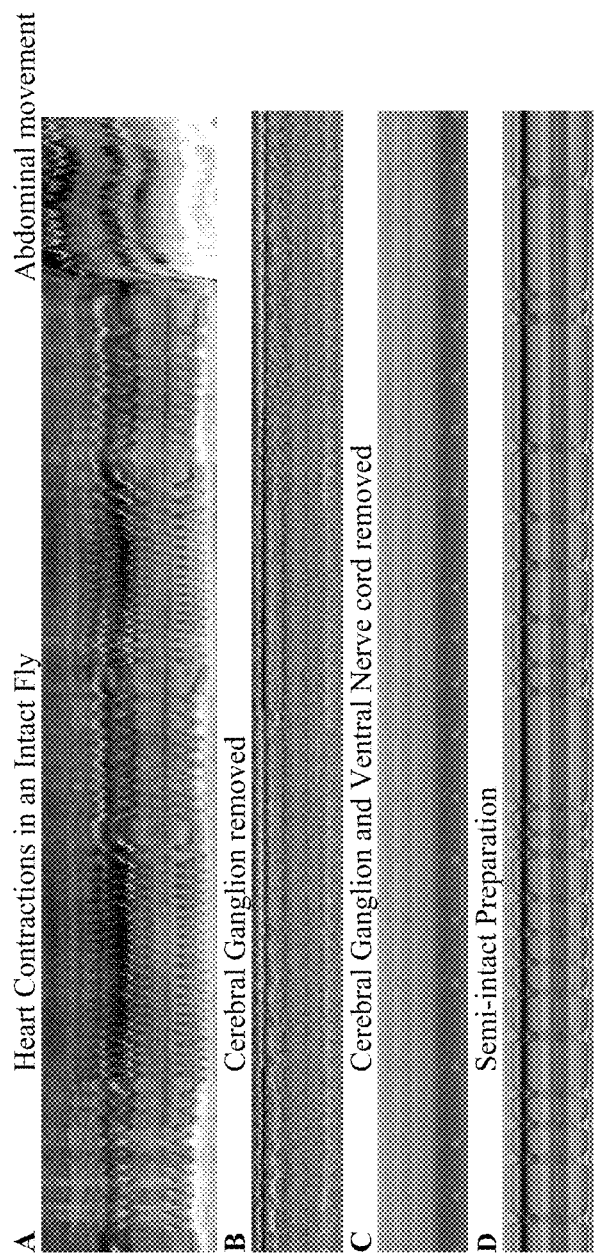
FIG. 1 shows the effects on M-mode patterns obtained from exposed hearts following removal of fat bodies. (A) An M-mode pattern from an intact fly showing movement due to contractions in the heart and abdomen (15 s record). (B) M-mode of heart contractions following removal of the head (cerebral ganglia) (10 s record). (C) 10 s M-mode of heart contractions following removal of the both head (cerebral ganglia) and ventral thorax (ventral nerve cord). (D) 10 s M-mode of heart tube contractions from a semi-intact preparation. (B-D are from the same 3 week old fly.)

The following definitions and methods are provided to better define the present invention and to guide those of ordinary skill in the art in the practice of the present invention. Unless otherwise noted, terms are to be understood according to conventional usage by those of ordinary skill in the relevant art. We have developed novel semi-intact *Drosophila* heart preparations and image analysis methods for monitoring inherent myogenic activity and determining the effects of various cardioactive drugs and genetic variants on heart function.

Novel *Drosophila* Heart Preparations

This model system is a powerful approach for elucidating the roles of ion channels in heart function, heart aging, and heart disease. Importantly, this system with a complement of channels similar to humans, can be used as a drug testing model. Further, studies of ion channels are possible using a fly heart engineered to express human ion channel genes.

Antiarrhythmia drugs such as clofilium or ibutilide have been shown to induce arrhythmias in some patients. Other drugs such as antihistamines have also been shown to cause arrhythmias. These are thought to be due to drug effects on both HERG and KCNQ channels. Both of these channels are present in the fly heart and application of clofilium and ibutilide can induce arrhythmias in the fly. Thus, this system can be used to screen for possible drug side effects.

Applicability of the Image Analysis Methods to Other Model Systems

The image analysis methods of the present invention can be used to analyze any small heart that can be visualized and recorded. In addition, it can be used to analyze images of larger hearts, such as, for example, an echocardiogram the human heart.

For example, we have successfully applied our detection algorithm to zebrafish larva. This is another increasingly genetically tractable model system that has a two chamber heart which undergoes looping as does the human heart. In the larva the heart is still linear and can be analyzed as the fly heart. Thus this detection system should prove useful to describe the effects of genes on the developmentally of the heart and heart function in this system.

We have also successfully applied this detection system to mouse embryonic heart. This is another increasingly genetically tractable system that is possesses a four chamber heart very similar to human heart in morphology. It should be noted that this system is less useful for drug testing as many if not most of the cardioactive drugs target the HERG and KCNQ ion channels which do not play a large role in heart contractions in rodent models.

Finally our algorithm can be applied to echocardiograms to provide information about arrhythmicity in human heart function. All of the parameters that can be measured in the *Drosophila* model (heart period, diastolic and systolic intervals, fractional shortening and arrhythmicity, for example) can be obtained from analysis of an echocardiogram.

The image analysis methods of the present invention compare changes in overall frame intensity as well as individual pixel density from one image to the next. As a result, any set of images in a sequence of images can be analyzed. The "cruder" frame brightness algorithm differentiates between the systole and diastole, while the pixel intensity change algorithm sensitively detects any movement, although it does not distinguish between the movement as the heart contracts and the movement as it relaxes. By combining the two algorithms, very sensitive motion detection is obtained together with the ability to independently and simultaneously identify the overall state of the heart (contracted versus relaxed).

The present invention will be further described by the following nonlimiting examples.

EXAMPLES

Example 1

KCNQ Potassium Channel Mutations Cause Cardiac Arrhythmias in *Drosophila* that Mimic the Effects of Aging This example, which is provided as background information, is from Ocorr et al., Proc. Natl. Acad. USA 104:3943-3948, 2007, which is herein incorporated by reference in its entirety. Supplementary material was provided at www.pnas.org/cgi/content/full/0609278104/DC1, which is also incorporated herein by reference in its entirety.

Materials and Methods

Image Analysis and M-Mode Traces on Semi-Intact Preparations.

Flies were anaesthetized with fly nap for 2-5 min and the head, ventral thorax and ventral abdominal cuticle were removed exposing the abdomen. All internal organs except the heart were removed as well as any abdominal fat. Dissections were done under oxygenated AHL. These semi-intact preparations were allowed to equilibrate with oxygenation for 15-20 min prior to filming. All procedures were done at room temperature (18-22° C.). Hearts exposed by this procedure typically beat rhythmically for up to four hours and have been observed beating as long as eight hours post dissection. Analysis of flies that express GFP specifically in neuronal membranes showed that the peripheral neural input to the conical chamber and the portion of the heart tube in the third abdominal segment was consistently disrupted by the dissection procedure.

Image analysis of heart contractions was performed using high speed movies of semi-intact *Drosophila* preparations. Movies were taken at rates of 100-200 frames per second using a Hamamatsu EM-CCD digital camera on a Leica DM LFSA microscope with a 10× water immersion lens. In order to get a random sampling of the heart function from the flies, a single 10 s recording was made for each fly without previewing. All images were acquired and contrast enhanced using Simple PCI imaging software (Compix, Inc.). M-modes were generated using either the Simple PCI software or a MatLab-based image analysis program written by one of the authors. Briefly, a 1 pixel-wide region is defined in a single frame of the movie that encompasses both edges of the heart tube; identical regions are then cut from all of the frames in the movie and aligned horizontally. This provides an edge trace that documents the movement of the heart tube edges in the y axis over time in the x axis.

Measurements of diastolic and systolic diameters as well as diastolic and systolic intervals were obtained either from direct measurements of M-mode traces or as output from the MatLab-based program. The incidence of fibrillation in flies was automatically detected by quantifying systolic intervals longer than 0.5 s or diastolic intervals less than 0.06 s. The systolic value was chosen because systoles that have clearly definable contraction and relaxation phases were never seen to last longer than 0.4 s and the maximal average systolic interval in wildtype flies was 0.4 s in 5 week old flies. The diastolic interval cutoff was roughly half the shortest, regularly occurring diastolic interval observed in all the semi-intact preparations, which was 0.13 s. Thus any detected relaxations lasting less than 0.06 s were most likely incomplete and were fibrillatory in nature. The incidence of asystoles was determined by quantifying all diastolic intervals lasting longer than 1.3 s. This value was approximately twice the average diastolic interval for all wildtype flies examined and was longer than any of the intervals measured for 1 and 3 week old wildtype flies. Significant differences were determined by Analysis of Covariance (ANCOVA) and two-tailed independent samples T-test where appropriate; p values less than 0.05 were considered significant.

Results

Fruit flies have an open circulatory system with a linear heart tube located along the dorsal midline in the abdomen and a aorta that extends anteriorly into the head region (Wessels et al., Nat. Genet. 36:1275-1281, 2004; Rizki, in *The Genetics and Biology of Drosophila*, ed. Wright [Academic Press, London], pp. 1839-1845, 1978; Curtis et al., J. Morphol. 240:225-235, 1999; Molina and Cripps, Mech. Dev. 109:51-59, 2001). There are four sets of internal valves that divide the abdominal heart into an anterior conical chamber and three posterior compartments (Monier et al., Development 132:5283-5293, 2005). Each of the four heart compartments also contains a pair of valves to the exterior, called ostia, which permit hemolymph to enter and leave the heart (Rizki, in *The Genetics and Biology of Drosophila*, ed. Wright (Academic Press, London), pp. 1839-1845, 1978).

KCNQ Gene Expression in Fly Hearts.

To study the heart-related function of the *Drosophila* KCNQ gene, deletion mutants were generated by imprecise excision of a transposable element (EP2074). In the following analysis two alleles ($KCNQ^{186}$ and $KCNQ^{370}$) deleting all transmembrane domains including the potassium selective pore region of the KCNQ channel were used. A precise excision of the inserted EP2074 element ($KCNQ^{97}$) served as the wildtype control. Both deletion alleles are homozygous viable and fertile without any detectable visible defects, except that mutant larvae (compared to $KCNQ^{97}$) take 1-2 days longer to develop, fewer enclose, and the mean lifespan in females is reduced 20-30%. KCNQ transcripts are first expressed in the embryo at mid-embryonic stages primarily in the nervous system, but not yet in the heart. In the adult, KCNQ is expressed at high levels in the head but also in other tissues including the anterior as well as the posterior portion of the heart. RT-PCR of adult flies and isolated hearts shows absence of 5' (and transmembrane) KCNQ RNA in KCNQ$^{186}$ and KCNQ$^{370}$ mutants, compared to KCNQ$^{97}$ wildtype control or compared to transcripts corresponding to the 3' KCNQ region.

A recent report shows that $K_{ATP}$ channel associated dSUR RNA levels of the adult heart decline dramatically with age (Akasaka et al., Proc. Natl. Acad. Sci. USA 103:11999-20004, 2006). To explore whether KCNQ expression also changes with age we assessed the KCNQ RNA levels of isolated hearts with qRT-PCR at one week and five weeks of age. Indeed, we find that KCNQ RNA declines dramatically with age; RNA levels at five weeks are one third of those seen at one week.

Pacing-Induced Cardiac Dysfunction is Elevated in KCNQ Mutants.

In humans the effects of loss of function mutations in the KCNQ gene are more pronounced under conditions of physical or emotional stress (Schwartz et al., Circulation 83:1171-1180, 1991). Cardiac stress in humans, induced by exercise and electrical pacing, coupled with echocardiography is a useful tool in the detection of certain forms of disease (reviewed in Gligorova and Agrusta, Cardiovasc. Ultrasound 3:36, 2005). To gauge cardiac performance in *Drosophila*, we used an external electrical pacing paradigm to physically stress the fly heart by accelerating its baseline rate of 3-4 Hz, to 6 Hz for 30 seconds (Wessels et al., Nat. Genet. 36:1275-1281, 2004; Wessels and Bodmer, Biotechniques 37:58-60, 2004). Immediately following the pacing regime we visually assessed heart performance; heart dysfunction manifests as temporary or permanent heart arrest (reminiscent of human sudden death syndromes) or uncoordinated twitching. The fraction of young, 1-week old wildtype and KCNQ$^{97}$ control hearts that exhibit such cardiac dysfunction is relatively low (20-30% "failure rate"), as previously reported (Wessels et al., Nat. Genet. 36:1275-1281, 2004). By comparison the incidence of pacing-induced cardiac dysfunction in age-matched KCNQ$^{186}$ and KCNQ$^{370}$ mutants is drastically increased (70-80%). These elevated rates seen in young KCNQ mutant flies were as high as those observed in aged, 5-week old KCNQ$^{97}$ control flies and other wildtype strains (Wessels et al., Nat. Genet. 36:1275-1281, 2004). The elevated "failure" rates seen in young KCNQ mutant flies did not increase further with age suggesting that that cardiac performance in these flies is already significantly compromised due to the absence of KCNQ channel function.

Since the heart rate in *Drosophila* can be modulated by neuronal input (Dulcis and Levine, J. Neurosci. 25:271-280, 2005) and because KCNQ is also expressed in the nervous system, we wanted to examine whether the increased incidence in cardiac dysfunction observed in mutant flies could be rescued by overexpressing the wildtype KCNQ gene specifically in the mesoderm, which includes the heart. Using the UAS-Gal4 system (Brand and Perrimon, Development 118:401-415, 1993), control and KCNQ deletion mutants were combined with either the 24B-Gal4 mesodermal driver or a UAS-KCNQ gene and then crossed together. The incidence of pacing-induced cardiac dysfunction of KCNQ deletion mutants expressing the wildtype KCNQ cDNA was similar to the control KCNQ$^{97}$ combinations and was significantly reduced compared to KCNQ mutant flies. Similar results were obtained for a duplicate set of crosses with an independent UAS-KCNQ insertion. These results suggest that KCNQ is likely required autonomously within the heart muscle to establish normal cardiac performance.

Increased Incidence of Heart Arrhythmias in KCNQ Mutant Flies.

Pacing-induced cardiac failure is indicative of cardiac dysfunction but it does not provide information as to the specific underlying causes or mechanisms. In order to further characterize the heart's contractile properties we captured heart wall movements in individual flies using a high speed digital video camera. Movies of normally beating hearts taken through the cuticle of intact flies were used to generate M-mode traces that display the dynamics of heart tube contraction. These traces show the position of the heart wall edges (Y axis) over time (X axis). Heart beat frequencies in intact flies showed alternations between faster and slower rates, probably due to neuronal and hormonal input as has been previously described (Dulcis and Levine, J. Neurosci. 25:271-280, 2005; Johnson et al., J. Insect Physiol. 46:1229-1236, 2000; Dulcis et al., J. Neurobiol. 64:259-274, 2005). To study the inherent myogenic contraction parameters without confounding influences from neuronal input, we developed a semi-intact fly preparation in which the heart is surgically exposed and most neuronal inputs to the heart are disrupted. M-modes from movies of these semi-intact heart preparations from young, 1-week old flies (yw, w$^{1118}$ and KCNQ$^{97}$, all considered "wildtype", wt) show regular rhythmic contractions lasting for over an hour in oxygenated supplemented artificial hemolymph. The highly rhythmic beating pattern deteriorates as flies age and by 5-7 weeks a majority of wildtype flies exhibit non-rhythmical heart contraction patterns, including asystoles/bradycardias and fibrillations/tachyarrhythmias.

In contrast to wildtype flies, M-mode records from KCNQ mutant hearts exhibit severely non-rhythmic beating patterns already at young ages. When we quantified the incidence of all types of aberrant heart beat within random, 10-second M-mode traces, we found that both KCNQ mutant lines displayed elevated levels of arrhythmia at young ages when compared to controls and the incidence of arrhythmia increased more rapidly with age in mutants. In addition, there appeared to be an age-dependent increase in the severity of the rhythmicity defects in mutant flies beyond those seen in aged wildtype flies. We developed an image analysis program that allowed us to objectively measure a number of heart parameters. We quantified the length of systolic and diastolic intervals, as well as heart cycle lengths or periodicity, defined as the length of time between the ends of two consecutive diastolic intervals. In semi-intact wildtype heart preparations the average heart period increases moderately with age, as previously reported (Wessels et al., Nat. Genet. 36:1275-1281, 2004; Paternostro et al., Circ. Res. 88:1053-1058, 2001). In contrast, KCNQ mutant flies exhibit a dramatic age-dependent increase of the heart period compared to age-matched controls (p<0.05). When we monitored separately the two components of the heart period, diastole (DI) and systole (SI), we find that in KCNQ mutant flies both DI and SI show age-dependent increases.

We explored whether the irregularities observed in the mutant heart rhythms were reflected in an increased variability of the heart periodicity. Using the standard deviation of the heart period as an "arrhythmia index", we find that this quantitative measure of rhythmicity reflects well the heart rhythm disturbances observed in M-mode traces. In wildtype control flies the cardiac arrhythmia index increases progressively with age, from about 0.1 at one week to 0.4 at seven weeks of age. The arrhythmia index for KCNQ mutant hearts is roughly double that of the controls at most ages examined. Thus, arrhythmias increase with age in both wildtype and mutants, but much more rapidly in KCNQ flies.

In order to quantify the incidence of unsustained fibrillation/tachyarrhythmia we measured the number of SI that were unusually long (>0.5 s, indicative of sustained contractions) as well as the number of very short DI (<0.06 s, indicative of incomplete relaxations). Using these criteria we computed a significant elevation in the incidence of fibrillation events in both KCNQ mutants compared to controls, especially in young flies, reflecting the increase in unsustained fibrillations observed when visually inspecting in the M-mode records. The mean DI also tended to be longer in KCNQ flies when compared to age-matched controls. When we quantified unusually long DI (>1.3 s) as a measure of asystolic events we found a significant elevation in the incidence of asystoles in both KCNQ mutants compared to controls.

To further illustrate the differences in rhythmicity we plotted the distribution of SI and DI intervals for individual flies in histogram format. The majority of wildtype flies show relatively tight clustering of both DI and SI that persists until five weeks of age when the distributions broaden. KCNQ mutant flies, however, show a much more variable distribution at both young and old ages. In order to represent the increased incidence of unsustained fibrillation for all flies in a genotype we plotted the overall distribution of SI by normalizing the data for individual flies to the average median value. The median SI length in KCNQ mutant flies increases dramatically with age relative to wildtype and the incidence of very long SI, which indicate episodes of fibrillation, is higher in KCNQ mutant flies at all ages. Similar results are seen in plots of heart periodicity.

The alterations in rhythmicity observed for the KCNQ mutant flies can be rescued by supplying wildtype KCNQ channel function transgenically. We analyzed hearts from KCNQ mutant flies containing a wildtype UAS-KCNQ construct and the mesodermal 24B driver. In such 'mesodermal rescue' KCNQ flies the arrhythmia index is much reduced compared to UAS or 24B controls and is even below the wildtype level at three weeks of age. These results suggest that supplying functional KCNQ channels to the heart restores a regular heart rhythm in KCNQ mutants. In addition, heart-specific KCNQ overexpression in old wildtype flies reverses the age-dependent increase in arrhythmias. This is consistent with the idea that the age-dependent decrease in KCNQ expression within the heart contributes to the increased incidence of arrhythmia observed with age.

Electrophysiological Analysis of Fly Heart Function.

We used a multi-electrode array system to monitor field potentials from dissected heart preparations of wildtype and KCNQ mutant flies. Recordings from beating hearts in wildtype flies showed positive deflections followed immediately by negative deflections that correlated with heart contraction and relaxation respectively. In KCNQ mutants the negative deflections did not immediately follow the initial positive potentials and usually occurred with significant delay compared to field potentials from wildtype hearts, consistent with the increases in SI observed in KCNQ mutants. This result is consistent with a reduced ability of the heart to repolarize presumably due to the decrease in the repolarizing $K^+$ currents of the cardiomyocytes in KCNQ mutant flies. Thus, the role of KCNQ channels in *Drosophila* cardiomyocytes is remarkably similar to that in vertebrates.

Muscle Tension Measurements.

Muscle tension was measured as an indicator of muscle function in semi-intact fly heart preparations. Baseline tension measurements from wild-type hearts showed spontaneous regular contractions. Electrical stimulation (5-10 msec at 5 Hz) induced tachycardia and elevated diastolic tension. In wild type flies, the heart rate and systolic tension immediately decreased to baseline levels after cessation of stimulation. In contrast, contractions in KCNQ mutant hearts occurred at lower rates and with longer SI. In response to electrical stimulation, KCNQ hearts exhibited fibrillation, markedly elevated diastolic tension, and extremely delayed recovery to baseline diastolic tension relative to wildtype hearts. These results indicate that the heart muscle fibers from KCNQ mutant flies have a markedly reduced ability to relax following contractions, consistent with the "diastolic dysfunctions" commonly found in various types of cardiomyopathy in humans (Maurer et al., J. Am. Coll. Cardiol. 44:1543-1549, 2004).

Discussion

Outward currents through KCNQ channels can contribute to the waveform and rhythmic contractions in at least two types of vertebrate muscle cells, heart muscle (Sanguinetti et al., Nature 384:80-83, 1996) and portal vein smooth muscle (Yeung and Greenwood, Br. J. Pharmacol. 146:585-595, 2005). Repolarization in the *Drosophila* heart also appears to depend on outward $K^+$ currents that are mediated, in part, by KCNQ channels. Mutations in the pore-forming region of this channel result in an increase in heart arrhythmias, which are manifest as an increased variation of the heart period ('arrhythmia index'), including episodes of unsustained fibrillation/tachyarrhythmia in young flies. This increased incidence in arrhythmias also correlates with an increase in pacing-induced cardiac dysfunction (heart failure) in young KCNQ mutant flies. It is likely that both the increased incidence of arrhythmias and the decreased ability to withstand (pacing-induced) stress arise from the reduced ability of the myocardium to repolarize. The fact that hearts from old wildtype flies behave similarly to the hearts of young KCNQ mutants suggests that a decrease in repolarization reserve, due to decreased $K^+$ channel function, may be one of the molecular changes underlying age-related heart dysfunction. Our observation that KCNQ expression decreases with age and that replenishing KCNQ function in old flies apparently rejuvenates cardiac function is consistent with this hypothesis. Interestingly, clinical studies in humans and a recent study in flies suggest that activation of the ATP-sensitive $K^+$ channel in heart muscle is also attenuated with age (Akasaka et al., Proc. Natl. Acad. Sci. USA 103:11999-20004, 2006; Lee et al., Circulation 105:334-340, 2002). However, this channel is thought to have a cardioprotective role against hypoxia by slowing the heart rate, and does not appear to function during the normal heart contraction (Zingman et al., Proc. Natl. Acad. Sci. USA 99:13278-13283, 2002; Senio and Miki, Prog. Biophys. Mol. Biol. 81:133-176, 2003).

The progressively arrhythmic M-mode patterns seen in aging flies are reminiscent of the increased incidence of cardiac arrhythmic activities, e.g. atrial fibrillation, observed in aging humans (Wolf et al., Stroke 22:983-988, 1991; reviewed in Thom et al., Circulation 113:e-85-151, 2006; Lakatta, Heart Fail. Review 7:29-49, 2002; Lakatta, Heart Lung Circ. 11:76-91, 2002). Thus, the environmental and genetic modifiers that affect cardiac function in aging humans may also affect cardiac function in the *Drosophila* system. The identification of these modifiers will be critical to a molecular understanding of heart disease and of the effects of aging. Our findings that the incidence of cardiac arrhythmia in the hearts of KCNQ mutants occurs earlier than in wildtype flies and increases with age suggest that alterations in these and other channels involved in heart muscle repolarization may be responsible for some of the effects of aging on heart function. Furthermore, the ability to rescue these age-related defects by overexpressing wildtype KCNQ channels in mutant flies suggests that increases in the repolarization capacity of aging hearts may exert a protective effect against other age-related changes.

The conservation of genes and gene function between *Drosophila* and vertebrates, including humans, has repeatedly been documented. This similarity is likely to extend to heart function since the complement of ion channels that are expressed in the heart includes many of the same channels found in the vertebrate heart (Bodmer et al., in *Comprehensive Insect Science*, ed. Gilbert et al. (Elsevier, Amsterdam), Vol. 2, pp. 199; Akasaka et al., Proc. Natl. Acad. Sci. USA 103:11999-20004, 2006; Lalevee et al., Curr. Biol. 16:1502-1508, 2006). Remarkably, the regularity of the heart rhythm critically depends on properly functioning KCNQ channels from flies to humans, and these channels seem to play equivalent roles in basic cardiac myocyte physiology. Homologs of other ion channels associated with human arrhythmias, such as of Human Ether-a-Go-Go-Related Gene (HERG), also appear to produce arrhythmia in fly hearts. Mesodermal RNAi knock-down of seizure (the fly homolog of HERG) and mutants in ether-a-go-go (eag$^1$) produce non-sustained and sustained fibrillations/tacharrhythmias in semi-intact preparations.

At least one other human heart condition, dilated cardiomyopathy, has also been observed in flies (Wolf et al., Proc. Natl. Acad. Sci. USA 103:1394-1399, 2006). Here, we report a second cardiac condition, arrhythmias of the heartbeat, also exists in flies, and aberrant KCNQ function contributes to this condition. Arrhythmias in flies increase dramatically with age, as does the incidence in atrial fibrillation in the elderly (Wolf et al., Stroke 22:983-988, 1991) suggesting that the age-dependent changes in molecular constituents within the fly heart may also be conserved. The fly heart promises not only to provide clues as to the roles of (new) genes in aging and disease but also to provide a physiological model that is more complex than cultured myocytes and simpler and easier to study than is the vertebrate heart. The ability to combine genetic manipulation and physiological assays in a system that has a short life span makes *Drosophila* an attractive model in which to study the genetics of age-related changes in heart function and heart disease.

Example 2

Intact *Drosophila* Heart Preparations

Initial attempts to examine and quantify heart movements in the fly focused on optically recording heart movements through the dorsal cuticle. Although it is possible to visualize movement in this manner, analysis of the recordings was usually hampered by the presence of fat bodies that surround the heart and obscure its edges in most adult flies. A second problem with this approach is the complexity of the heart contraction patterns as a result of nervous input and abdominal movements (FIG. 1). Such patterns of heart tube contractions have been described previously (Dulcis and Levine, J. Neurosci 25:271-280, 2005). This more complex pattern reverts to a simpler, more regular myogenic pattern following removal of both the head and ventral thorax which also removes the ventral nerve cord.

We have discovered that final disruption of nervous input is achieved with disruption of the nerve bundles that innervate the heart during fat removal.

Flies are placed, dorsal side down, into a smear of Vaseline®. This allows for movement of the fly during dissection without tearing the cuticle, which occurs when using conventional minuten pins and Sylgard-filled dissecting dishes. The head and ventral thorax are removed with a single cut and the tip of the posterior abdomen is also cut using irridectomy scissors. At this point the preparation is covered with an adult artificial hemolymph that attempts to mimic the ionic composition and osmolarity reported for hemolymph for adult flies (Wang et al., Cell 112:271-282, 2004; and Singleton and Woodruff, Dev. Biol. 161:154-167, 1994). The composition of the artificial hemolymph is $NaCl_2$ (108 mM), KCl (5 mM), $CaCl_2$ (2 mM), $MgCl_2$ (8 mM), $NaH_2PO_4$ (1 mM), $NaHCO_3$ (4 mM), HEPES (15 mM), sucrose (10 mM), trehalose (5 mM), pH 7.1.

The ventral cuticle is removed by cutting along the lateral edge on both sides of the abdomen using the hole made by the posterior cut as an access point. After removing the ventral cuticle the internal organs can generally be removed by simply grabbing the intestine with forceps and gently tugging (the anterior and posterior connections of the gut having been severed by the two cuts described above). The heart and surrounding fat, which lies on the dorsal cuticle, are now exposed.

In order to clearly view the edges of the heart tube it is critical to remove the fat, which usually partially overlies the heart and is opaque in the light microscope. This cannot be done using conventional dissecting tools such as forceps and scissors because the fat cells are generally not cohesive enough. Fat removal is accomplished using a suction technique that employs a finely drawn glass capillary and suction (using standard house vacuum). The diameter of the capillary controls the pressure and should be approximately 10-15 microns to allow for adequate suction of fat cells without damaging the nearby heart muscle cells. Care must be taken not to touch the heart during any part of this dissection as any contact will usually cause irreversible damage.

Example 3

Heart Movement Detection Algorithms

As described in the Examples above, we have developed a *Drosophila* heart physiology preparation that allows us to quantify and describe a number of parameters that are important in heart function. This methodology combines high speed optical recording of beating hearts with a robust, semi-automated analysis algorithm that is able to quantify heart beat parameters such as heart rate, diastolic and systolic intervals, systolic and diastolic diameters, percent fractional shortening, and contraction wave velocity on a beat-to-beat basis. In addition, our algorithm quantifies cardiac arrhythmicity, which increases as flies age. Our algorithm was also able to analyze optical recordings of hearts from larval zebrafish and 8d mouse embryos. Using this methodology we were able to document age-dependent changes in heart function in to different laboratory fly strains (yw and w$^{1118}$). We were also able to detect effects of a single mutant allele on heart function in tbx5 heterozygote mutant zebrafish. Our methodology for quantifying parameters of cardiac function in these genetically tractable model systems should provide valuable insights into the genetics of heart function.

INTRODUCTION

As described in above, we have developed a methodology for analyzing contraction-relaxation parameters in the myogenic heart of *Drosophila* that is also applicable to other model systems. Our method combines a denervated, exposed fly heart with a unique set of movement detection algorithms that automatically and precisely detect and measure heart parameters on a beat-to-beat basis providing both analytical and statistical power.

Recently, several groups have begun to examine heart function in the fruit fly with the goal of using this system as a physiological model that can be manipulated genetically (Ocorr et al., "Genetic control of heart function and aging in *Drosophila*," Trends Cardiovasc. Med. 17, 2007; Wolf et al., Proc. Natl. Acad. Sci. USA 103:1394-1399, 2006; Dulcis and Levine, J. Neurosci. 25:271-280, 2005; Wessels and Bodmer, Biotechniques 37:2-7, 2004). As in vertebrates, the fly heart exhibits myogenic pacemaker activity and it resembles the early embryonic human heart in that it is a linear tube with four chambers. Importantly, genetic manipulations of ion channel genes in *Drosophila*, including L-type $Ca^{2+}$ channels and several types of $K^+$ channels, suggest that the currents contributing to heart function in flies are remarkably similar to those in human hearts (Ocorr et al., "Genetic control of heart function and aging in *Drosophila*," Trends Cardiovasc. Med. 17, 2007; Gu and Singh, J. Neurobiol. 28:269-280, 1995; Dowse et al., J. Neurogenet. 10: 153-168, 1995; Johnson et al., J. Comp. Physiol. [B] 167:89-97, 1997; reviewed in Bodmer et al., "Heart Development and Function," p. 199-250. In Gilbert et al. (Ed.), *Comprehensive Insect Science*, Elsevier, Amsterdam, 2005).

A number of different methods have been developed to detect and quantify heart rate in fruit flies including: manual counting, detection of light intensity changes (5, 9-14), MESA (maximum entropy spectral analysis) (Johnson et al., J. Comp. Physiol. [B] 172:227-236, 2002; Sanyal et al., J. Comp. Physiol. [B] 176:253-263, 2006), recording electrical activity (Papaefthmiou and Theophilidis, In Vitro Cell Dev. Biol. Anim. 37:445-449, 2001), edge tracing in pupae (Wessells and Bodmer, Biotechniques 37:58-60, 2004), and optical coherence tomography (Johnston et al., Genome Biol. 5:R19, 2004). Most of these algorithms provide either (i) spectral analysis of the heart rate for long time periods, or (ii) beat-to-beat measurements for only about 2 seconds (i.e. for a total of 6 beats) with a maximal resolution of only 30 frames per second (fps), or (iii) require expensive equipment with presently limited spatial resolution (i.e. OCT).

In order to expand the characterization of *Drosophila* heart function, we developed an analytical package that combines two movement detection algorithms applied to optical recordings from exposed fly heart. The output provides more accurate and detailed information concerning pacemaker activity and contraction-relaxation parameters such as heart rate, including systolic intervals (SI) and diastolic intervals (DI), systolic and diastolic diameters, percent fractional shortening, heart rhythmicity, and contraction wave velocity (CWV) along the heart tube. We have also used these movement detection algorithms to quantify heart beat parameters in larval zebrafish hearts as well as embryonic mouse hearts.

Materials and Methods

Semi-Intact *Drosophila* Heart Preparation.

Flies were maintained and aged as described previously (Wessells and Bodmer, Biotechniques 37:58-60, 2004; Ocorr et al., Proc. Natl. Acad. Sci. USA 104:3943-3948, 2007). Abdominal heart tubes were exposed by first cutting off the head and ventral thorax of the fly and then removing the ventral abdominal cuticle and all internal organs. Dissections were performed under an artificial adult hemolymph (Based on Wang et al., Cell 112:271-282, 2004; and Singleton and Woodruff, Dev. Biol. 161:154-167, 1994) and contained $NaCl_2$ (108 mM), KCl (5 mM), $CaCl_2$ (2 mM), $MgCl_2$ (8 mM), $NaH_2PO_4$ (1 mM), $NaHCO_3$ (4 mM), HEPES (15 mM), sucrose (10 mM), trehalose (5 mM), pH 7.1. Image recordings of heart activity were acquired from semi-intact *Drosophila* preparations using a Hamamatsu EM-CCD digital camera (McBain Instruments, Chatsworth, Calif.) mounted on a Leica DM LFSA microscope with a 10× water immersion lens (McBain Instruments, Chatsworth, Calif.) and Simple PCI image capture software (Compix Imaging System, Selwicky, Pa.). All recordings were done at room temperature. Frame rates were 100-150 fps; all movies were 60 s in length.

Detection and Quantification of Movement Due to Heart Contractions.

Figure 3:
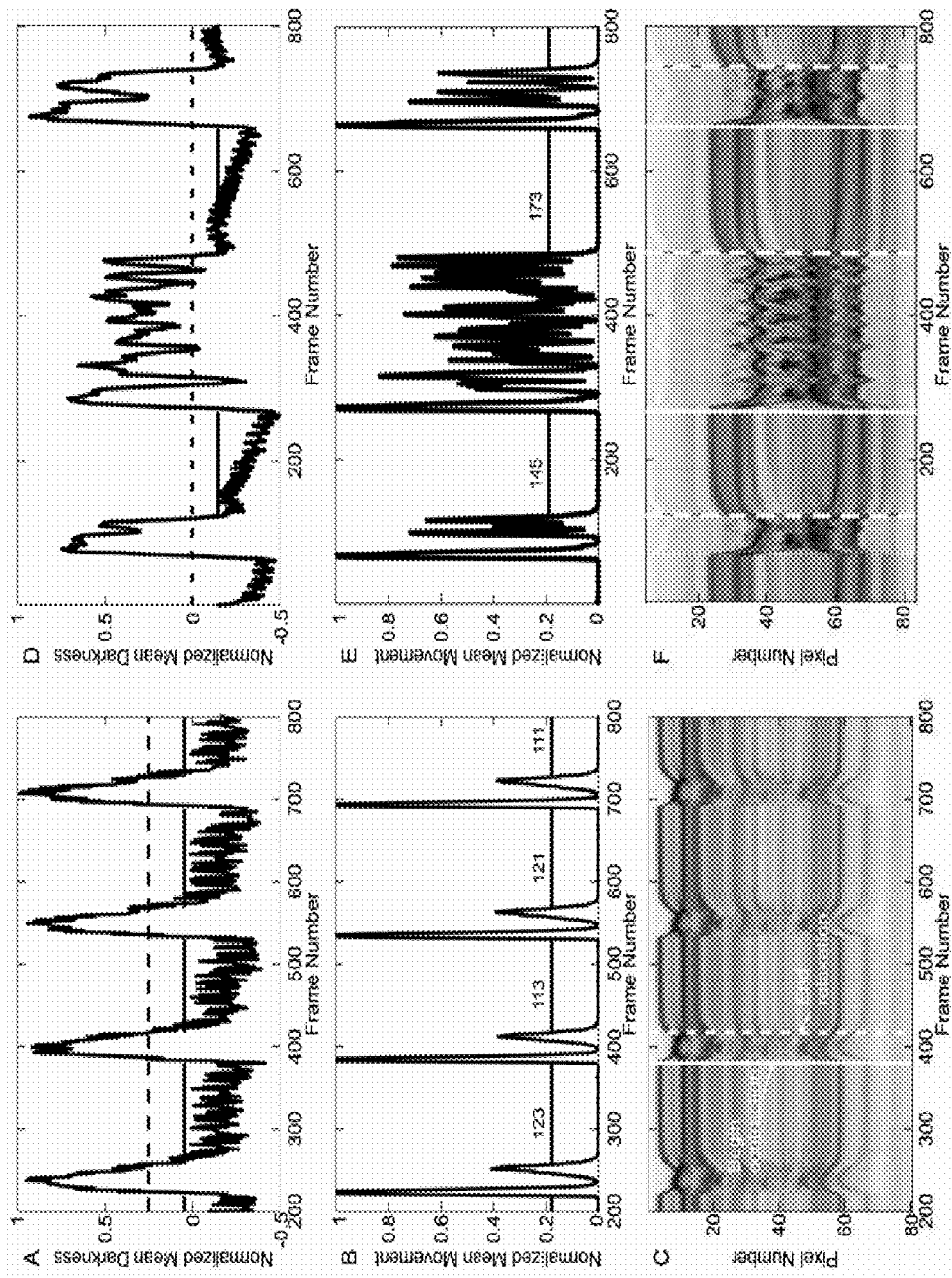
FIG. 3 shows movement detection from high-speed digital movies. (A) Movement detection using the Mean Frame Brightness algorithm for a 1 week old fly (left) and a 7 week old fly (right). (B) Movement detection using the Changing Pixel Intensity algorithm for a 1 week old fly (left) and a 7 week old fly (right). For each beat the first peak represents the movement due to contraction, whereas the second (or additional) movement is due to relaxation. The number of frames for each detected diastolic interval is printed above the horizontal line. (C) Movement detection using the Mean Frame Brightness algorithm for a 7 week old fly. (D) Movement detection using the Changing Pixel Intensity algorithm for a 7 week old fly, note incomplete relaxations/non-sustained fibrillations.

We used a combination of two movement detection algorithms written in Matlab® (The MathWorks, Inc.) to accurately track movement of the heart edges. The first approach tracks changes in average light intensity of each frame (FIG. 3A); this "Frame Brightness" algorithm (described below) reflects heart movement in some but not all of the movies. This approach has been employed previously using lower speed devices (Johnson et al., J. Comp. Physiol. [B] 167:89-97, 1997; White et al., J. Comp. Physiol. [B] 162:278-283, 1992; Paternostro et al., Circ. Res. 88:1053-1058, 2001; Ashton et al., Genetics 157:283-294, 2001, Sanyal et al., J. Comp. Physiol. [B] 176:253-263, 2006) to detect and quantify heart rate in *Drosophila*. The second approach detects movement by comparing the intensity changes in individual pixels from one frame to the next (FIG. 3B). This "Changing Pixel Intensity" algorithm (described below) is able to accurately detect even small heart wall movements. Our program also tracks heart movements by creating an M-mode similar to techniques used previously for analyzing echocardiograms for humans (Gowda et al., Int. J. Cardiol. 97:1-6, 2004).

Frame Brightness Algorithm.

For our semi-intact *Drosophila* heart preparation frame brightness decreases during the contractions because as the heart muscle cells contract the contractile proteins and cell membranes become more concentrated and obscure more of the transmitted light (FIG. 3A). To derive brightness changes, our algorithm first calculates the mean brightness value of all the pixels in a frame, then the output is normalized to the interval [0, 1] (FIG. 3A). Any low-frequency oscillations in the signal due to fluctuations in background illumination can be removed later by the user using a high-pass-filter.

Changing Pixel Intensity Algorithm.

During heart contractions the darker pixels, corresponding to the edges of the heart tube and associated tissues, move over the lighter background pixels. Movement can be detected reliably by locating areas where there are significant brightness changes between consecutive movie frames. To determine the areas in the movie which are "moving" between frames, we first calculate the relative brightness change (RBC) for each pixel in a frame relative to the previous frame (RBC=abs(pixelvalue(frame+1)−pixelvalue(frame))/(pixelvalue(frame)+1)). The maximum RBC in each frame represents therefore either the movement of a part of the darker membrane over bright background or, in the absence of any movement, the background noise. Our experience shows that the background noise for each movie shows little variability and thus we can use the minimum value of all the maximum RBCs in a movie as a threshold to consistently remove the background noise. Therefore, a pixel is considered to be "changing" or "moving" from one frame to the other if the RBC for that pixel is larger than the threshold determined by the background noise. The number of changing pixels per frame is normalized to the interval [0, 1] to get comparable results for each movie (FIG. 3B). To illustrate the results of this algorithm we can enhance the original movie by coloring all the detected, or "moving", pixels in red. This algorithm is sensitive enough to be able to discriminate a biphasic movement signal due to both the contraction and the relaxation movements with minimal noise (FIG. 3B).

Quantification of Heart Rate, DI and SI.

Three different thresholds can be adjusted by the user to refine and verify DI and SI detection as well as to remove artifacts (FIG. 3A and FIG. 3B). A first estimate of the timing and length of diastole (DI) is derived by setting a movement threshold (MT, FIG. 3B) relative to the movement traces. The pause in movement occurring during relaxation is quantified as the DI. The heart period (HP) is quantified as the time between the ends of two consecutive DIs, and SI is quantified as the HP minus the DI. The heart rate is calculated as the inverse of the HP.

For heart beats where contractions are relatively prolonged the algorithm does not always correctly identify the pause during contraction (i.e., an interval with no movement) as part of the SI. In this case information from the Frame Brightness Algorithm can be used to inform the Changing Pixel Intensity Algorithm as to what state the heart is in (I.E. contracted v. relaxed condition). Specifically, an upper threshold (dashed line, FIG. 3A) can be set such that movie frame sequences with a mean darkness level higher than the threshold will not be designated as a diastolic interval. A second brightness limit (solid line, FIG. 3A) can also be set that ignores movie frame sequences that have a mean darkness level below this threshold even though the darkness levels may be changing (IE. noise). To ensure that both the movement and brightness signals agree with the actual information from the movie the corresponding edge tracings, or M-modes, showing the movement of the heart tube edges can be displayed below the movement traces. M-modes are made by electronically selecting a single vertical row of pixels that spans the heart tube and electronically cutting out the same pixels from every frame in the movie and aligning them horizontally. This provides an image of the vertical movement of the heart tube edges (y axis) with time (x axis). M-modes can also be generated as a separate image file and provides a qualitative display of heart tube movements.

Output data for HP, DI, and SI is provided in a comma separated value file and includes the average, median, and standard deviation of all the contractions in each movie. We can also compare the individual HP, DI, and SI data for all recorded contractions from all individuals in a group. However, due to the variability in overall heart rate between individuals we normalize the data so that the median periods for the different data sets match up (each set is divided by its median value and multiplied by the group mean). Plots of this data then provide an overview of the distribution of these events).

Measurement of Heart Diameter.

In intact flies the edges of the heart tube are typically obscured by both the pigmented cuticle and abdominal fat bodies. However, in the semi-intact preparation where some of the fat cells can be removed the edges of the heart tube are usually visible in the region of the third abdominal segment. Thus it is possible to mark the edges of the heart within 1-2 pixels (~3µ). Movies can be advanced manually and two sets of points corresponding to the upper and lower borders of the heart tube can be marked in single frames during maximal relaxation and contraction. Conversion from pixels to microns is dependent upon calibration settings for the individual microscope and objective. Diastolic and systolic diameters can be used to calculate the percent fractional shortening (% FS=(Diastolic diameter−Systolic diameter)/Diastolic diameter), providing an estimate of the contractility of the heart tube. The program permits duplicate sets of measurements to be taken in which case the % FS is based on the average of each set of points.

Contraction Wave Velocity.

In all movies the heart tube is oriented along the horizontal axis with the anterior end to the left. Therefore, contraction waves progress along the horizontal axis of the movie frame and there is a measurable delay between the time when the contraction movement is detected on one side of the frame and the time when it occurs on the opposite side. An obvious parameter to measure is the contraction wave velocity (CWV). This is accomplished by calculating the mean movement level for 10 vertical strips of pixels across each movie frame and then selecting the two regions that are furthest apart horizontally and where the averaged signal level is at least 20% of the maximal movement signal.

Figure 4:
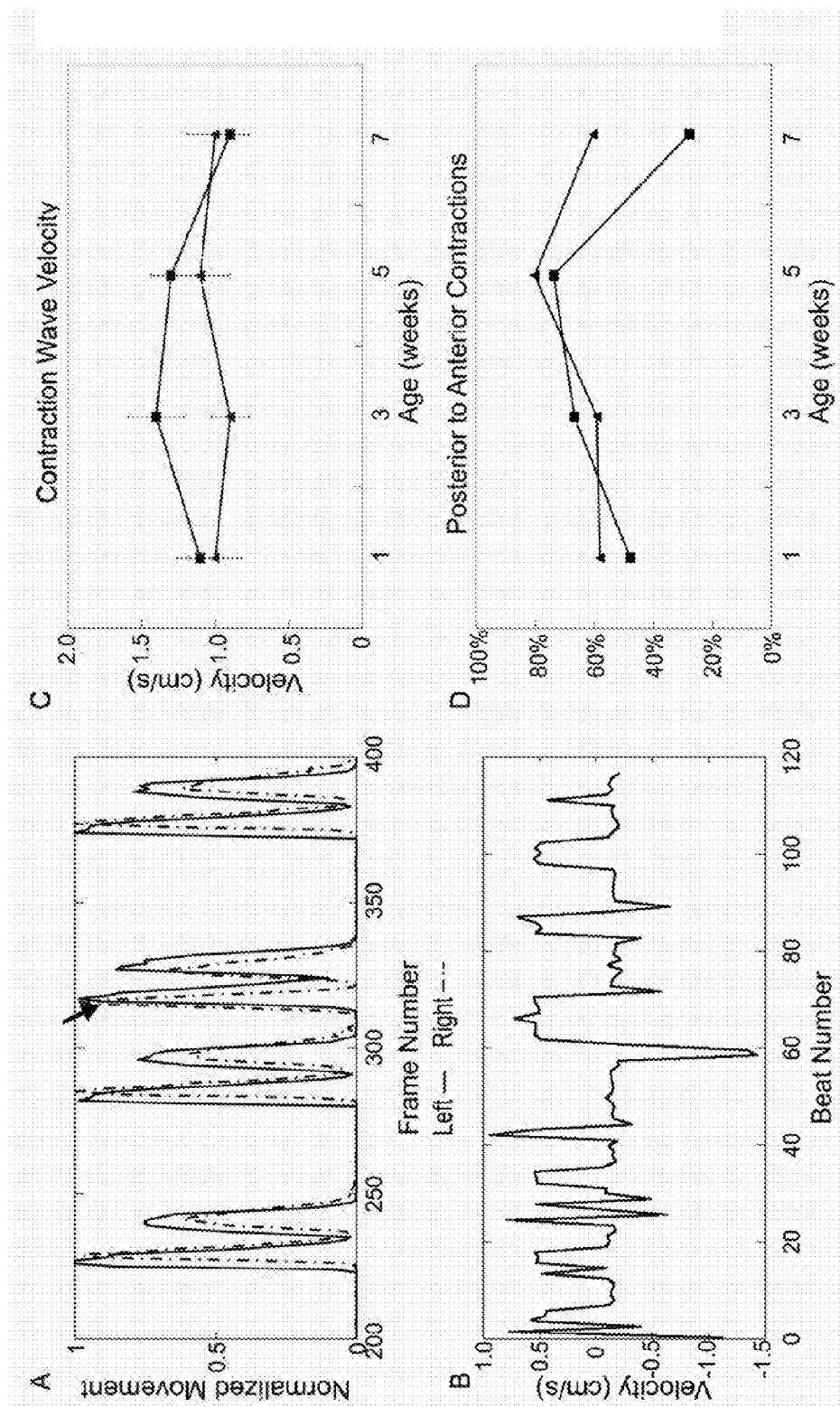
FIG. 4 shows the determination of contraction wave velocity. (A) Local movement detection traces generated at two separate locations in the movie frame are shown. Contraction wave velocity is determined by dividing the distance between the two detection points by the time separating the beginning of contraction in each location. A reversal in pumping direction is indicated by the arrow. (B) Instantaneous contraction velocities during a 60 s movie showing reversals in pumping direction. (C) The velocity of retrograde (posterior to anterior) heart muscle contractions (Mean±SEM, N=17-30 flies per data point). For C & D: ■yw, . . . ▲$w^{1118}$. (D) The percentage of total contractions that proceed in a retrograde (posterior to anterior) direction showing an increase with age up to 5 weeks.

The algorithm for deriving the velocity uses the mean movement signal (where the movement signal equals the user-defined MT and has a positive slope (see FIG. 4A) to find time points when a contraction movement occurs in each of the selected regions. The distance in pixels between the two regions is converted into a distance in microns based on the movie resolution and microscope calibration. Velocity is calculated using the time difference between movement signals in each region and the distance between them (FIG. 4B).

The adult fly heart has two pacemaker regions, one at the anterior and one at the posterior end of the abdominal heart tube. The overall direction of contraction is determined by whichever pacemaker region is dominant (Dulcis and Levine, J. Neurosci. 25:271-280, 2005). Consequently we also characterize the contraction wave according to the direction of the contraction: left-to-right (anterior-to-posterior or retrograde) and right-to-left (posterior-to-anterior or anterograde) (FIG. 4C and FIG. 4D).

Estimates for Rhythmicity and Abnormal Heart Contractions.

Figure 5:
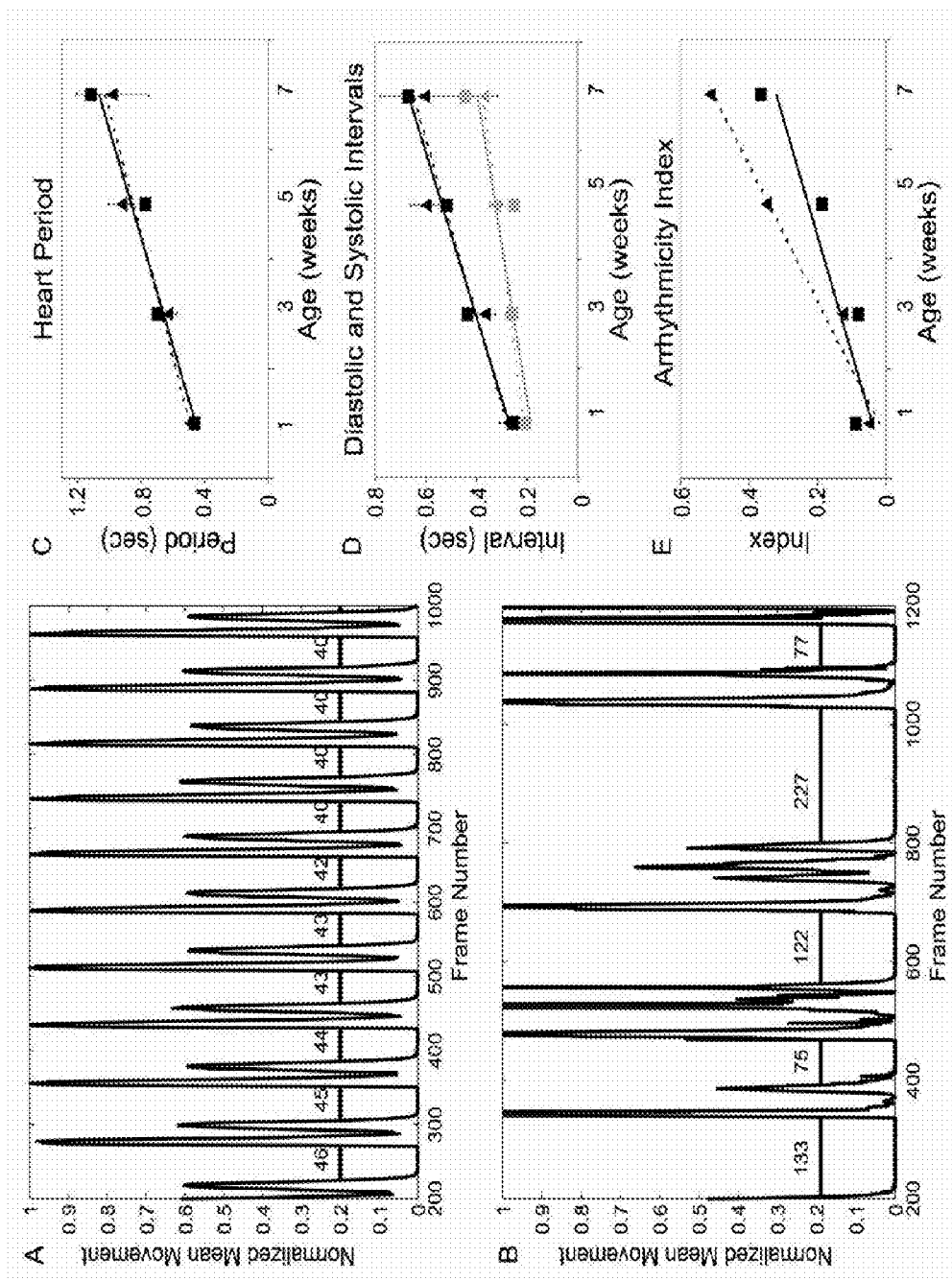
FIG. 5 shows heart beat intervals and quantification of arrhythmicity. (A) Movement trace showing DI detection (horizontal lines between movement peaks). Duration of the DI is given as the number of frames between successive movement traces; note the regularity of DI in this young (1 week old) fly. (B) Movement trace from an old fly (5 weeks) showing increased irregularity of both systolic and diastolic interval lengths. (C) Changes in heart period with age (Mean±SEM, 17-30 flies per data point). For C-E: ■yw, . . . ▲$w^{1118}$. (D) Diastolic intervals (black lines) and systolic intervals (gray lines) as a function of age (Mean±SEM, 17-30 flies/data point). (E) "Arrhythmicity Index" (AI) calculated as the heart period standard deviation normalized to the median heart period. Data points represent the average AI for all the flies in each age group (17-30 flies/data point). The age-dependent increase in AI reflects the observed increase in arrhythmic events that occurs as flies age (shown qualitatively in FIG. 2C). *$p<0.05$

As flies age the HP, DI, and SI all lengthen and become more variable; in addition many mutations also produce irregular heart rhythms (FIG. 5A-D, [Ocorr et al., Proc. Natl. Acad. Sci. USA 104:3943-3948, 2007]). We use two approaches to quantify the occurrence of specific types of arrhythmicities. One method depends on an estimation of the number of "long" DIs and SIs. Because the measured heart beat parameters are very reproducible for the two different wt strains at different ages we set specific time intervals for detecting very long or very short heart beat intervals. DIs longer than 1 s were considered prolonged (bradychardia); this value is approximately three times the length of the average DI in regularly beating hearts from young flies (FIG. 5D). Similarly, we detect unsustained fibrillation/tachyarrhythmia as the number of SI that were unusually long (>0.5 s), indicative of sustained contractions. This threshold is twice the average SI, a parameter that showed very little variability in young wt flies (FIG. 5D). We also include long SIs that were interrupted by very short DIs (<0.06 s, indicative of incomplete relaxations) in this measure.

A second method uses the standard deviation of the HP measurements for each fly as a measure of the heart rate variability (see Ocorr et al., Proc. Natl. Acad. Sci. USA 104: 3943-3948, 2007). We refer to this measure as the Arrhythmia Index (AI, FIG. 5E) and it increases progressively with age. In order to compensate for effects on periodicity due to long pauses, or prolonged contractions, we normalize this measure to the median HP. This is because the median value is less affected by extreme values (outliers) than is the mean thus it provides a more accurate representation of the "normal" value of the HP.

Results

An overview of the derived parameters for both *Drosophila* wildtype lines can be found in Table 1 below (see also Ocorr et al., Proc. Natl. Acad. Sci. USA 104:3943-3948, 2007.

TABLE 1

Summary of the statistical output from our analysis for young (1 week) and old (7 week) wt flies.

|  | w | | yw | |
| --- | --- | --- | --- | --- |
| Age | 1 week | 7 weeks | 1 week | 7 weeks |
| N | 34 | 24 | 30 | 22 |
| Heart Rate mean (Hz) | 2.20 | 1.56 | 3.042 | 1.26 |
| Heart Rate median | 2.19 | 1.53 | 2.49 | 1.18 |
| Heart Rate std | 0.16 | 0.32 | 0.35 | 0.40 |
| Heart Period mean (sec) | .50 | 1.01 | 0.46 | 1.11 |
| Heart Period median | 0.50 | 0.93 | 0.45 | 1.06 |
| Heart Period std (Normalized to Median HP) | 0.09 | 0.42 | 0.17 | 0.33 |
| Diastolic Interval mean (sec) | 0.30 | 0.60 | 0.26 | 0.67 |
| Diastolic Interval median | 0.3 | 0.56 | 0.25 | 0.63 |
| Diastolic Interval std | 0.14 | 0.41 | 0.08 | 0.32 |
| Systolic Interval mean (sec) | 0.20 | 0.41 | 0.21 | 0.45 |
| Systolic Interval median | 0.21 | 0.38 | 0.21 | 0.42 |
| Systolic Interval std | 0.014 | 0.14 | 0.02 | 0.15 |
| Diastolic Diameter (microns) | 72.3 | 63.0 | 80.8 | 57.7 |
| Systolic Diameter (microns) | 43.6 | 39.5 | 48.4 | 38.3 |
| Fractional Shortening | 40% | 36% | 40% | 33% |
| Anterograde Contractions (% of Total Beats, Left to right) | 49% | 42% | 52% | 71% |
| Anterograde Velocity (cm/sec) | 0.89 | 1.04 | 1.00 | 1.16 |
| Retrograde Contractions (% of Total Beats, Right to left) | 51% | 58% | 48% | 29% |
| Retrograde Velocity (cm/sec) | 0.99 | 0.87 | 1.05 | 0.92 |

*Drosophila* Semi-Intact Preparation.

While it is possible to record movements in the anterior portion of the heart in intact flies, M-modes prepared from these movies illustrate the complexity of heart beat patterns in intact flies. As previously reported (Dulcis and Levine, J. Neurosci. 25:271-280, 2005), input from the nervous system dramatically alters the heart rate and overall level of contractility. Removing the head (and hence the cerebral ganglia) has little effect on the M-mode patterns, but removing the thoracic ventral nerve cord (which includes the subesophageal ganglion) results in a more regular pattern that is reminiscent of the patterns seen in the denervated semi-intact preparation.

The semi-intact preparation functions well in situ for hours following dissection. Heart parameters such as HP, DI, SI, and % FS show a remarkable similarity between flies and all remain extremely stable for at least 4 hours, even in relatively elderly (4 week old) fly preparations supplied with oxygenated, trehalose-supplemented artificial hemolymph. Since all optical recordings are typically performed between 30-60 minutes following dissection the data generated by our optical method reflects the function of a stable myogenic heart tube.

Using this preparation we are able to document a number of changes that occur in the *Drosophila* heart with age. HP increases significantly with age in wt flies (FIG. 5C, Table 1), consistent with previous observations (Ocorr et al., Proc. Natl. Acad. Sci. USA 104:3943-3948, 2007; Wessells et al., Nat. Genet. 36:1275-1281, 2004) and we are also able to document that this is due to a highly significant increase in the DI with age ($p<0.001$) as well as a smaller but significant increase in SI with age ($p<0.001$, FIG. 5D and Table 1). With age the heart beat patterns also become more disorganized and include periods of fibrillation/tachycardia and asystole/bradycardia and this is reflected in an increase in the numbers of prolonged diastoles and sustained systoles that are detected. Results from our automated detection method suggest that it underestimates the arrhythmicity in heart beat contraction patterns when they become increasingly disorganized. The average AI (Arrhythmia Index), which is based on the variability of the individual heart periods in a record, also exhibits a significant increase with age (FIG. 5E, ANCOVA, $p<0.002$) that reflects the age-related increase in arrhythmicity seen in M-mode traces.

To check the accuracy of the interval detection algorithm we randomly selected 10 movies of 3 week old flies and compared manual measurements with the output of our algorithm. Manual measurements for DI and SI were obtained using M-modes in which three representative diastolic and systolic intervals were measured and averaged for each fly. Interval lengths were calculated as # pixels (1 pixel=1 movie frame) divided by the frames per second. The results we obtained were similar to those generated by our program for both DI (manual=0.43±0.07 s, automated=0.40±0.07 s, Mean±S.E.M.) and SI (manual=0.24±0.05 s, automatic=0.29±0.04 s, Mean±S.E.M.).

Measurements of Heart Diameters and Fractional Shortening.

Diastolic and systolic diameters represent the relaxed and contracted state of the heart tube respectively. Values for diastolic and systolic diameters are relatively constant for a given location throughout a movie but may vary according to the region of the heart (along the anterior-posterior axis). Typically the conical chamber (anterior) region has a greater diameter than do more posterior regions. For comparative purposes all measurements were made at the same location for all flies in a region of the heart tube that is relatively linear (abdominal segment #3). The average diameters systolic and diastolic measured from sample frames of movies are remarkably similar for both strains of wt flies (FIG. 2A) and are very similar to previously reported results (Ocorr et al., Proc. Natl. Acad. Sci. USA 104:3943-3948, 2007). In addition, the measurements appear to be sensitive enough to document small, statistically significant decreases in size for both wt strains with age ($p<0.01$).

Indicators for excitation-contraction coupling are strength and duration of the contraction. Measurements of heart tube size in both contracted and relaxed states were used to generate an estimate of the volume of hemolymph ejected per longitudinal unit and, indirectly, the strength of the contraction. This measure is the percent fractional shortening which declines slightly but significantly with age ($p<0.01$, FIG. 2B, Table 1).

Propagation Velocity of the Contraction Wave.

Detection of the contraction wave velocity (CWV) is based on a comparison of the movement signal at automatically detected regions at the borders of the movies. FIG. 4A shows movement traces generated at the left and right borders of each frame from a single movie. The average CWV for all ages of wildtype flies we examined is 1.1±0.2 cm/s (mean±S.D.). The data available for the left ventricle long axis contraction wave exhibited peak velocities of 8-14 cm/s (Vinereanu et al., Echocardiography (Mount Kisco, N.Y.) 19:177-185, 2002). The algorithm also detects changes in directionality as heart beats with negative velocity (see the third beat in FIG. 4A, also FIG. 4B). CWV did not appear to depend upon directionality of contraction; the posterior to anterior velocity was 1.1±0.2 cm/s compared to an anterior to posterior velocity of 1.0±0.2 cm/s.

Applicability of Motion Detection Algorithms to Larval Zebrafish and Mouse Hearts.

We have used our motion detection algorithms to analyze heart movies from two additional model systems: the zebrafish and the mouse.

Larval Zebrafish Hearts.

Two to three day old zebrafish have a linear tube that starts to loop forming an anterior ventricle and a posterior atrium; because they are transparent at this stage, heart contractions can be filmed from intact, immobilized larva. Ventricular contractions proved the easiest to analyze. Movies were taken with anterior to the left of the field and dorsal on the bottom; in this position the ventricle is quite prominent and the program typically tracks the more exaggerated movement exhibited by the dorsal portion of the ventricle.

Figure 6:
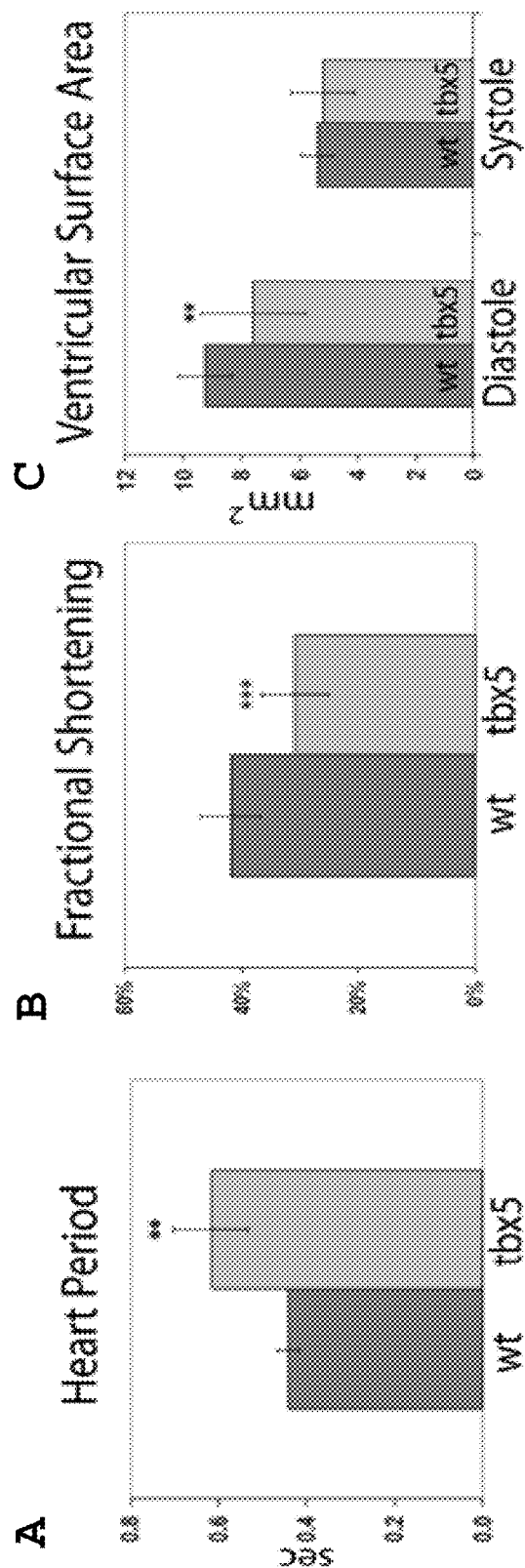
FIG. 6 shows zebrafish heart parameters. 10 second M-modes were obtained from three day old zebrafish movies. Wild-type M-modes showed regular heart contractions as evidenced by the significant movement of the heart edge in the dorsal region of the heart. All tbx5 heterozygotes showed aberrations in their m-mode traces, primarily characterized by more prolonged contractions with heart wall movements that were noticeably less robust and less fluid. Contraction traces and corresponding M-modes were obtained from a wild-type zebrafish showing the correlation between the pixel by pixel movement detection algorithm and the movements of the heart wall. (A) Heart period was measured as the interval between the start of one diastole and the beginning of the next. Heart periods were measured for every beat in each movie and averaged for each fish. Results for 16 wildtype and 27 tbx5 heterozygote zebrafish show a significant reduction in the heart period in heterozygotes compared to controls (B) Fractional shortening was measured as the percent change in the ventricular surface area between diastole and systole. Heart measurements were made only if all heart edges were clearly visible in the movie frames. Results from 15 wildtype and 12 tbx5 heterozygotes show a significant reduction in the % fractional shortening in heterozygotes compared to controls. (C) A comparison of the ventricular surface areas of hearts measured in (B) during diastole and systole indicate that the decrease in % fractional shortening is due to a decrease in the diastolic size of the hearts. Diastolic surface area of tbx5 heterozygotes was significantly smaller than controls whereas systolic surface area did not differ significantly between the two groups. For (A), (B), and (C) results are given as mean±SEM. ($p<0.01$, *$p<0.0001$, unpaired, two-tailed t-test).

M-mode records show that contractions of the wildtype larval heart are somewhat different from those seen in the fly in that they do not exhibit a prolonged diastole. As seen in the fly heart, movement traces showed both contraction and relaxation peaks, however because the diastolic intervals were typically very short they were incorrectly identified as systolic intervals by the movement algorithm. When these traces are compared with the corresponding m-mode it is clear that the program inverts diastolic and systolic intervals. This may also be the result of differing reflectivity of the two preparations under our recording conditions. Nevertheless, interval measurements could still be made and the systolic interval output in the overview files was relabelled as the diastolic interval output (and vice versa). Using the output from our algorithms we were able to document a significant increase in the heart period (reduction in heart rate) in zebrafish larva that are heterozygote for a mutation in the tbx5 gene compared to controls (wt) (FIG. 6A, p=0.009). This increase is due primarily to a significant prolongation of the systolic interval in the mutant relative to wt (0.29±0.11 and 0.18±0.05 sec respectively, mean±S.D., p=0.004) as well as a smaller but still significant prolongation of the diastolic interval in the mutant relative to wt (0.33± and 0.26±sec respectively, mean±S.D., p=0.02).

Fractional shortening can also be estimated by measuring both the vertical and the horizontal dimensions of the hearts in both diastole and systole and then calculating the ventricular surface area based on the equation for an oval (a/2×b/2×π). This measure is significantly reduced in tbx5 heterozygotes (FIG. 6B, p=0.00002) indicating that that the output and contractility of their hearts are compromised even in tbx5 heterozygotes at very early stages of development. This reduction in heart contractility appears to be primarily the result of a selective reduction in the diastolic volume of the heart relative to wildtype hearts (FIG. 6C, p=0.005). This conclusion is also supported by the zebrafish M-mode data showing reduced and delayed ventricular contraction movements.

Embryonic Mouse Hearts.

We also analyzed hearts from 7.5-8d mouse embryos. Recordings were made from the left side of the embryo prior to looping while the heart tube is still relatively linear; in this position the ventricle is the most prominent heart structure. Embryos were surgically removed following cervical dislocation of the mother and were cultured for one hour in oxygenated DMEM at 37° C. prior to optical recording. Heart contractions at this stage are easily tracked by the Changing Pixel Intensity algorithm and resemble the contraction/relaxation patterns seen in flies. The output from our analysis showed an average heart rate of 1.4±0.12 Hz (mean±S.D.), which is higher than the 1 Hz rate typically obtained by visual observation of embryos in culture (Porter and Rivkees, Am. J. Physiol. Regulatory Integrative Comp. Physiol. 281:401-407, 2001). Ontogeny of humoral heart rate regulation in the embryonic mouse) but is lower than the 2.2 Hz obtained in vivo using doppler analysis of 8.5 d embryos (Ji et al., Circ. Res. 92:133-135, 2003; originally published online Jan. 16, 2003). In addition, our analysis permitted a determination of the relative DI (0.41+0.04 sec, mean±S.D.) and SI (0.32±0.03 sec, mean±S.D.).

Discussion

Our heart analysis algorithm can automatically detect, with great accuracy, both the onset of contraction and the end of relaxation providing precise measurements of DIs and SIs. This capability is due in part to that fact that our algorithm uses changes in individual pixel intensities for each movie frame to detect movement, providing a reliable and steady signal with very little noise. Equally important is the combined use of information from the light intensity signal and information from the movement signal. This combinatorial approach allows our algorithm to correctly discriminate between the movement pauses that occur during both contraction and relaxation, allowing us to accurately determine DI, SI, and thus heart rate, on a beat-by-beat basis throughout a large amount of data (see FIGS. 3 and 5).

Figure 2:
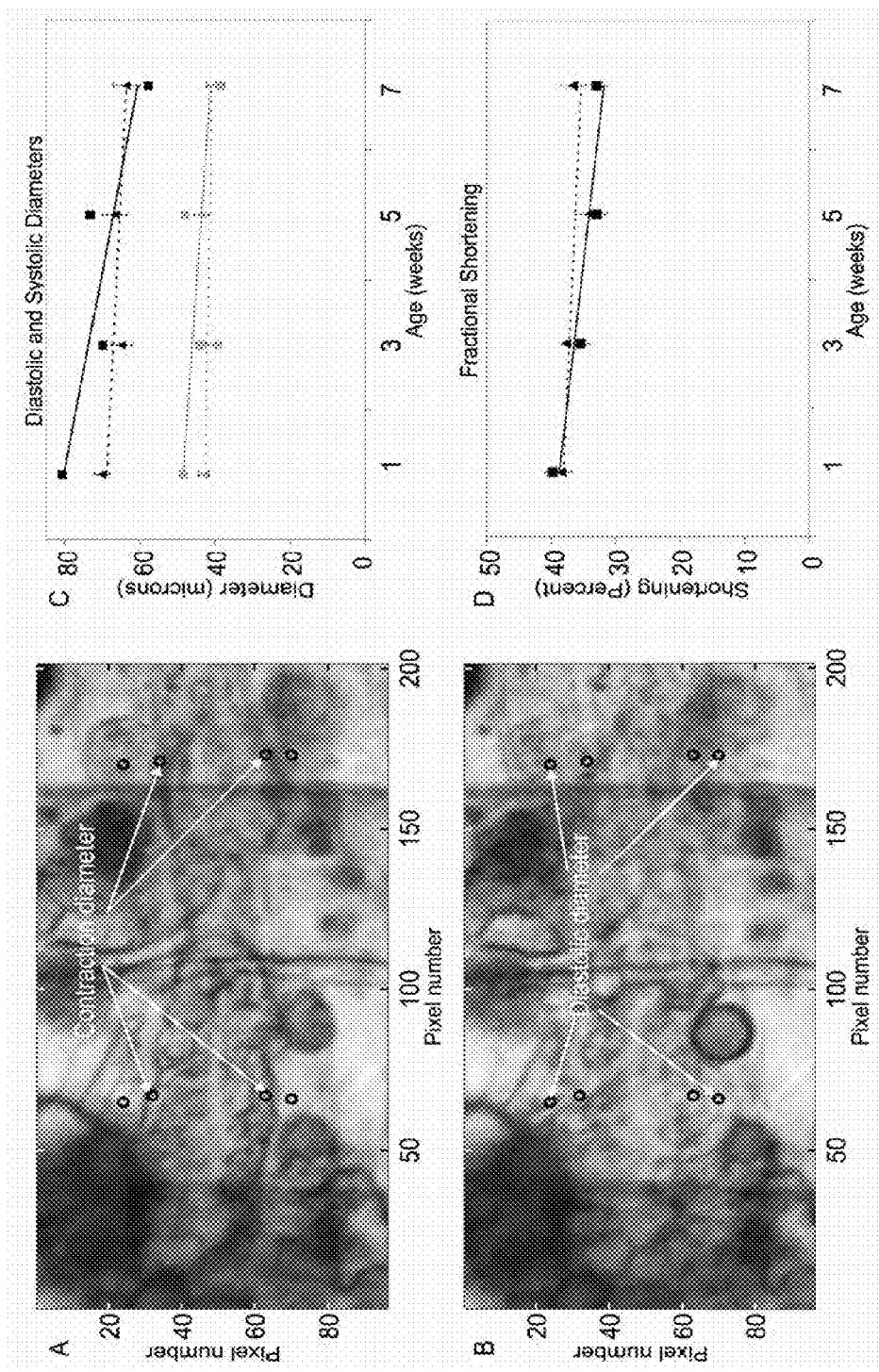
FIG. 2 shows systolic and diastolic heart diameters. Movie stills were taken of four segments in the fly abdomen showing the exposed heart during systole and of the same fly heart during diastole; positions were marked by the user and used by the program to calculate heart diameters. (A) Quantification of the diastolic and systolic diameter measurements for yw and $w^{1118}$ laboratory wildtype strains of *Drosophila*. Data points represent the mean (±SEM) for 17-30 flies per data point. (■yw, . . . ▲$w^{1118}$, black lines represent diastole, gray lines represent systole) (B) Percent fractional shortening (FS) provides an estimate of the ejection volume and is obtained from the data shown in A [(diastolic diameter−systolic diameter)/diastolic diameter)×100]. Note the decrease of FS with age due to the relatively greater increase of diastolic diameter versus systolic diameter. (■yw, . . . ▲$w^{1118}$)

Using this system we have been able to document age-related changes in the fly heart at a level of detail that provides insight into the physiological basis for these changes. For example, previous studies have shown that HR (the inverse HP) decreases with age in Drosophila and our data confirms these results (FIG. 5C). However, our methodology allows us to go beyond simply measuring HR; we are able to demonstrate that although the SI also increases slightly with age, the age-dependent decrease in HR is disproportionately due to increases in the DI (FIG. 5D). We also document age-dependent decreases in the fractional shortening or output of the heart (FIG. 2A and FIG. 2B). In addition, we have been able to quantify a more elusive characteristic, the degree of heart beat arrhythmicity. A visual examination of the movies and M-modes provides a qualitative picture of the "arrhythmicity" for individual flies (see Ocorr et al., Proc. Natl. Acad. Sci. USA 104:3943-3948, 2007). However, these results are difficult to express quantitatively and are not useful for comparing groups of individuals. By setting absolute boundaries (thresholds) for the DI and SI we can detect unusually long contractions and relaxations indicating arrhythmias. This method provides qualitatively similar results compared to manual estimations, however, it is clear that our automated detection underestimates the number of arrhythmic hearts. A better method for measuring arrhythmicity proves to be the normalized standard deviation of the HP ("Arrhythmicity Index", AI), a measure that quantifies the variability in the HP for each fly. The AI also showed significant increases with age in flies (FIG. 5E) but because this method is not limited to just detecting "long" diastoles or systoles it is likely to be a more flexible and accurate method for generally quantifying arrhythmias.

Interestingly, the age-dependent alterations in heart function that we observe in flies have correlates in humans. Age-dependent decreases in the intrinsic heart rate (e.g., Jose and Collison, Cardiovasc. Res. 4:160-167, 1970; Strobel et al., J. Interv. Card. Electrophysiol. 3:15-18, 1999) and increases in the incidence of heart arrhythmias have also been documented in humans (Thom et al., Circulation 113:e85-151, 2006; Furberg et al., Am. J. Cardiol. 74:236-241, 1994). More recently a $K^+$ channel (KCNQ), known to be involved in repolarization in the vertebrate heart, has been shown to be crucial for repolarization of the fly heart (Ocorr et al., Proc. Natl. Acad. Sci. USA 104:3943-3948, 2007). Furthermore, mutations in this channel are known to produce Torsades des Points arrhythmias in human hearts (Roden, Trends. Cardiovasc. Med. 14:112-116, 2004) and similar arrhythmic events are seen in KCNQ mutant fly hearts (Ocorr et al., Proc. Natl. Acad. Sci. USA 104:3943-3948, 2007). These results suggest that the fly heart may be a useful model for studying the cellular and molecular events underlying cardiac function and arrhythmia. This system for monitoring the physiology of fly heart function will allow us to take advantage of the powerful genetic tools that are already available in *Drosophila* to elucidate the genetics of cardiac function and cardiac aging.

Our algorithm is also able to quantify parameters in other heart preparations including larval zebrafish hearts and mouse embryos. We are able to show reductions in heart rate occurring as early as 2-3 days in zebrafish larva heterozygous for a mutation in the tbx5 gene. Previous studies relying on visual quantification of heart rate have shown that fish that are homozygous for mutations in the tbx5 gene cause bradycardia in zebrafish larva (Garrity et al., Development 129:4635-4645, 2002), but we are the first to document an effect on heart rate in fish that are heterozygous for the tbx5 mutation at an early stage of development. In addition, our results showing a reduced fractional shortening in zebrafish are consistent with the effects of tbx5 mutations on heart function in the mouse. Zhu et al. (unpublished) recently observed a significant reduction in the end diastolic diameters of hearts from adult tbx5 mutant mice and altered diastolic function and ventricular stiffness in young humans. Thus this system will be useful for quantifying heart function in model systems other than *Drosophila*.

REFERENCES

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method of analyzing heart movement comprising: (a) producing a plurality of optical images of the heart as it beats; (b) using a Frame Brightness algorithm to identify changes in overall light intensity in said plurality of optical images to determine whether the heart is in a contracted or relaxed condition; (c) detecting movement of the heart by comparing intensity changes in individual pixels from one of said plurality of said optical images to another of said optical images; and (d) identifying a pause between contraction and relaxation movements of the heart.

2. The method of claim 1 further comprising using a Changing Pixel Intensity algorithm to detect said movement of the heart by comparing intensity changes in individual pixels from one of said plurality of said optical images to another of said optical images.

3. The method of claim 2, wherein the output from the Frame Brightness algorithm is used to inform the Changing Pixel Intensity algorithm whether the heart is in the contracted or relaxed condition.

4. The method of claim 1, further comprising producing a movie of the heart as it beats, wherein the movie comprises said plurality of optical images.

5. The method of claim 2, further comprising determining a member selected from the group consisting of: heart period, heart rate, diastolic interval, systolic interval, standard deviation of heart period, standard deviation of heart rate, standard deviation of diastolic interval, standard deviation of systolic interval, percent fractional shortening of heart contraction, arrhythmia index, velocity of heart muscle contraction, and directionality of heart muscle contraction.

6. The method of claim 2 wherein the heart is selected from the group consisting of a *Drosophila* heart, a zebrafish larval heart, a mouse embryo heart, and a human heart.

7. The method of claim 6 wherein the heart is an excised, denervated *Drosophila* heart that retains myogenic activity.

\* \* \* \* \*